(12) United States Patent
Kobayashi et al.

(10) Patent No.: US 6,573,297 B2
(45) Date of Patent: Jun. 3, 2003

(54) (2-SUBSTITUTED OXYPHENYL) ALKANAMIDE DERIVATIVE, HAIR GROWTH PROMOTER AND EXTERNAL COMPOSITION FOR SKIN USING THE SAME

(75) Inventors: Koji Kobayashi, Kanagawa (JP); Hirotada Fukunishi, Kanagawa (JP); Tokuro Iwabuchi, Kanagawa (JP)

(73) Assignee: Shiseido Co., Ltd., Tokyo (JP)

( * ) Notice: Subject to any disclaimer, the term of this patent is extended or adjusted under 35 U.S.C. 154(b) by 39 days.

(21) Appl. No.: 09/984,202

(22) Filed: Oct. 29, 2001

(65) Prior Publication Data

US 2002/0052498 A1 May 2, 2002

Related U.S. Application Data

(62) Division of application No. 09/496,258, filed on Feb. 1, 2000.

(30) Foreign Application Priority Data

Feb. 4, 1999 (JP) .............................................. 11-27604

(51) Int. Cl.$^7$ .......................... A61K 31/16; C07C 69/00; C07C 261/00; C07C 233/00

(52) U.S. Cl. ........................ 514/490; 514/490; 514/489; 514/476; 514/625; 560/142; 560/136; 564/170

(58) Field of Search ................................. 514/490, 489, 514/476, 625; 560/142, 136; 564/170

(56) References Cited

FOREIGN PATENT DOCUMENTS

| | | |
|---|---|---|
| DE | 1116 680 | 11/1961 |
| DE | 25 40 552 A1 | 3/1976 |
| EP | 0 548 798 A1 | 8/1993 |
| EP | 0 911 320 A2 | 4/1999 |
| EP | 0 933 361 A1 | 8/1999 |
| EP | 0 940 390 A1 | 9/1999 |
| JP | 54142445 * | 6/1981 |
| WO | WO 95/17888 | 7/1995 |
| WO | WO 97/28141 | 8/1997 |

OTHER PUBLICATIONS

Japanese Patent Office, "Patent Abstracts of Japan," Publication No.: 08026942 A, Publication Date: Jan. 30, 1996, Application No.: 06180499, Application Filing Date: Jul. 11, 1994.
European Patent Office, "Patent Abstracts of Japan," Publication No.: 08026942, Publication Date: Jan. 30, 1996, Application No.: 06180499, Application Filing Date: Jul. 11, 1994 (as listed directly above).
Japanese Patent Office, "Patent Abstracts of Japan," Publication No.: 08020521 A, Publication Date: Jan. 23, 1996, Application No.: 06156226, Application Filing Date: Jul. 7, 1994.
Japanese Patent Office, "Patent Abstracts of Japan," Publication No.: 07316023 A, Publication Date: Dec. 5, 1995, Application No.: 06134879, Application Filing Date: May 26, 1994.
Japanese Patent Office, "Patent Abstracts of Japan," Publication No.: 07316022 A, Publication Date: Dec. 5, 1995, Application No.: 06109371, Application Filing Date: May 24, 1994.
European Patent Office, "Patent Abstracts of Japan," Publication No.: 07316022 A, Publication Date: Dec. 5, 1995, Application No.: 06109371, Application Filing Date: May 24, 1994 (as listed directly above).
Japanese Patent Office, "Patent Abstracts of Japan," Publication No.: 07304736 A, Publication Date: Nov. 21, 1995, Application No.: 06096347, Application Filing Date: May 10, 1994.

(List continued on next page.)

Primary Examiner—Richard L. Raymond
Assistant Examiner—Sudhaker B. Patel
(74) Attorney, Agent, or Firm—Snider & Associates; Ronald R. Snider

(57) ABSTRACT

A (2-substituted oxyphenyl)alkanamide derivative or a salt thereof expressed by the following Formula (I):

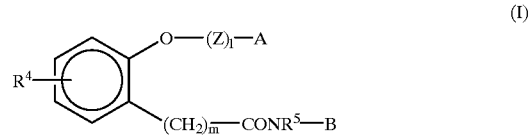

(I)

wherein one of A and B is a hydrocarbon group of $C_{3-30}$ expressed by $R^1$ and the other is $-(CH_2)n-NR^2R^3$; Z is $-CO-$ or $-CONR^6-$; $R^2$ and $R^3$ individually represent H, lower alkyl or benzyl, or $-NR^2R^3$ may be a heterocycle having 3–7 members; wherein $-CONR^5-(CH_2)n-NR^2R^3$ or $-CONR^6-(CH_2)n-NR^2R^3$ may be the following Group (II):

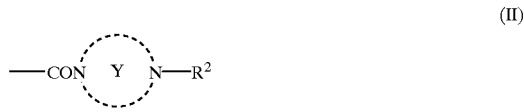

(II)

wherein ring Y is a heterocycle of 6 or 7 members; $R^4$ is selected from the group consisting of H, halogen, lower alkyl, lower acyl and etc; $R^5$ and $R^6$ are individually H, lower alkyl, lower acyl or lower alkylcarbamoyl, or may form a part of said Group(II); 1 is 0 or 1; m is 1 or 2; and n is an integer of 0–5. The (2-substituted oxyphenyl) alkanamide derivative or the salt thereof has excellent hair growth and regrowth promoting effects, which are useful for care, improvement or prevention of hair loss in mammals and, in particular, in human.

12 Claims, 7 Drawing Sheets

OTHER PUBLICATIONS

Papadaki–Valiraki et al., "Antidepressant effects of new (2,3–dialkoxyphenyl)methyl hydrazides and their N'benzyl derivatives on rats and mice," p. 98; col. 2; Chemical Abstracts, vol. 103, No. 25, Dec. 23, 1985, XP–002137401.

European Patent Office, "Patent Abstracts of Japan," Publication No.: 56065810, Publication Date: Jun. 3, 1981, Application No.: 54142445, Application Filing Date: Feb. 11, 1979.

Barton Holmquist et al., "Esterase Activity of Zinc Neutral Proteases," Biochemistry, vol. 15, No. 1, pp. 101–107, 1976 (month unknown) known, good filing date.

Japanese Patent Office, Japanese Unexamined Patent Publication No. 50–151885, Publication Date: Dec. 8, 1975, Application No.: 49–60480, Application Filing Date: May 29, 1974 (English language translation provided for a portion of this document).

* cited by examiner

Reaction Formula A

Reaction Formula B

Reaction Formula C

Reaction Formula D

Reaction Formula E

Reaction Formula F

(2-SUBSTITUTED OXYPHENYL) ALKANAMIDE DERIVATIVE, HAIR GROWTH PROMOTER AND EXTERNAL COMPOSITION FOR SKIN USING THE SAME

This application is a division of application Ser. No. 09/496,258, filed Feb. 1, 2000,

RELATED APPLICATIONS

This application claims the priority of Japanese Patent Application No. 11-27604 filed on Feb. 4, 1999, which is incorporated herein by reference.

FIELD OF THE INVENTION

The present invention relates to a (2-substituted oxyphenyl)alkanamide derivative and, in particular, to a (2-substituted oxyphenyl)alkanamide derivative that has excellent hair growth effect.

BACKGROUND OF THE INVENTION

At the present time, scalp abnormality due to activation of androgen in an organ such as hair root or sebaceous gland, lowering of blood stream toward hair follicle, excess secretion of sebum, formation of peroxide and the like has been considered as a cause of baldness or hair loss. Accordingly, a compound or composition that can remove or reduce the above-mentioned problems has been generally included into a hair growth promoting composition to promote hair growth and regrowth and to prevent hair loss, for a long time (in the present invention, "hair growth promoting composition" includes hair regrowth promoting composition, and the like).

At present, compounds or crude drug extracts having various functions have been compounded to the hair growth promoting composition. These functions include blood flow promoting action, topical stimulation, hair follicle activating action, antiandrogen action, antiseborrheic action and the like have been known. Examples of drugs having blood flow promoting action include swertia herb extract, vitamin E and its derivative, and benzyl nicotinate. Examples of drugs which promote blood circulation by topical stimulation include capsicum tincture, cantharides tincture, camphor and vanillic acid nonylamide. Examples of drugs having hair follicle activating action include hinokitiol, placental extract, photosensitizing dye, pantothenic acid and derivative thereof. Examples of drugs having antiandrogen action include estradiol and estrone. Examples of drugs having antiseborrheic action include sulfur, thioxolone and vitamin B6.

In addition to these drugs, salicylic acid, resorcine and the like that have corneocyte desquamating action and antibacterial action can be compounded to hair growth promoting composition for the purpose of preventing dandruff. Further, glycyrrhizic acid, menthol and the like can be compounded in order to prevent inflammation of scalp. Furthermore, amino acids, vitamins, extracts of crude drugs and the like can be compounded so as to aliment to hair follicle and activate enzyme activity.

Meanwhile, for example, D (L)-pantolactone (Unexamined Japanese Patent Publication No. Hei 8-26942), 2(1H)-pyridone derivative (Unexamined Japanese Patent Publication No. Hei 8-20521), $N^G$-nitro-L-arginine (Unexamined Japanese Patent Publication No. Hei 7-316023), 3-methyleneisoindolin-1-one derivative (Unexamined Japanese Patent Publication No. Hei 7-316022), indole derivative (Unexamined Japanese Patent Publication No. Hei 7-304736) are disclosed in recent patents as drugs having hair regrowth effect, hair growth effect, and hair loss protecting effect.

However, although the drugs described above are compounded to the conventional hair growth promoting compositions, they do not always exhibit sufficient hair regrowth and growth promoting effect.

SUMMARY OF THE INVENTION

In view of the foregoing problem in the prior art, an object of the present invention is to provide a compound, which is excellent in hair growth and regrowth promoting effect on human hair, and a hair growth promoting composition comprising the same as an active ingredient.

As a result of diligent studies of the inventors for attaining the above mentioned objects, it has been found that certain (2-substituted oxyphenyl)alkanamide derivative and its salt have excellent hair growth and regrowth promoting effect, thereby accomplishing the present invention.

Namely, a (2-substituted oxyphenyl)alkanamide derivative or a salt thereof in accordance with the present invention is expressed by the following Formula (I):

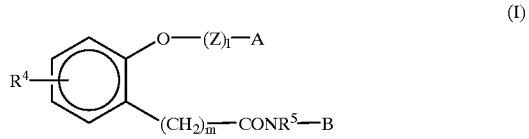

(I)

wherein each of A and B is $R^1$ or —$(CH_2)n$-$NR^2R^3$, wherein when A is $R^1$, B is —$(CH_2)n$-$NR^2R^3$ and when A is —$(CH_2)n$-$NR^2R^3$, B is $R^1$;

Z is —CO— or —$CONR^6$—;

$R^1$ is a hydrocarbon group of $C_{3-30}$;

$R^2$ and $R^3$ individually represent a hydrogen atom, a lower alkyl group or a benzyl group, or —$NR^2R^3$ may be a heterocycle having 3–7 members; wherein when B is —$(CH_2)n$—$NR^2R^3$ or when —$(Z)_1$—A is —$CONR^6$—$(CH_2)n$-$NR^2R^3$, said —$CONR^5$—$(CH_2)$ n-$NR^2R^3$ and said —$CONR^6$—$(CH_2)n$-$NR^2R^3$ may be expressed by the following Group (II):

(II)

wherein ring Y is a heterocycle of 6 or 7 members including two nitrogen atoms, and $R^2$ is a hydrogen atom, a lower alkyl group or a benzyl group;

$R^4$ is selected from the group consisting of a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R^5$ is a hydrogen atom, a lower alkyl group, a lower acyl group or a lower alkylcarbamoyl group; wherein when B is —$(CH_2)n$-$NR^2R^3$, —$CONR^5$—$(CH_2)n$-$NR^2R^3$ may be said Group (II);

$R^6$ is a hydrogen atom, a lower alkyl group, a lower acyl group or a lower alkylcarbamoyl group; wherein when $-(Z)_1-A$ is $-CONR^6-(CH_2)n-NR^2R^3$, $-CONR^6-(CH_2)n-NR^2R^3$ may be said Group (II);

l is 0 or 1;

m is 1 or 2; and n is an integer of 0–5.

A hair growth promoting composition in accordance with the present invention is characterized by comprising said (2-substituted oxyphenyl)alkanamide derivative or the pharmacologically acceptable salt thereof as an effective ingredient.

An external preparation for skin in accordance with the present invention is characterized by comprising said (2-substituted oxyphenyl)alkanamide derivative or the pharmacologically acceptable salt thereof.

A method for promoting hair growth in accordance with the present invention is characterized by applying an effective amount of said (2-substituted oxyphenyl)alkanamide derivative or the pharmacologically acceptable salt thereof on the skin of mammals and, in particular, on human scalp.

BEST MODE FOR CARRYING OUT THE INVENTION

Figure 1:
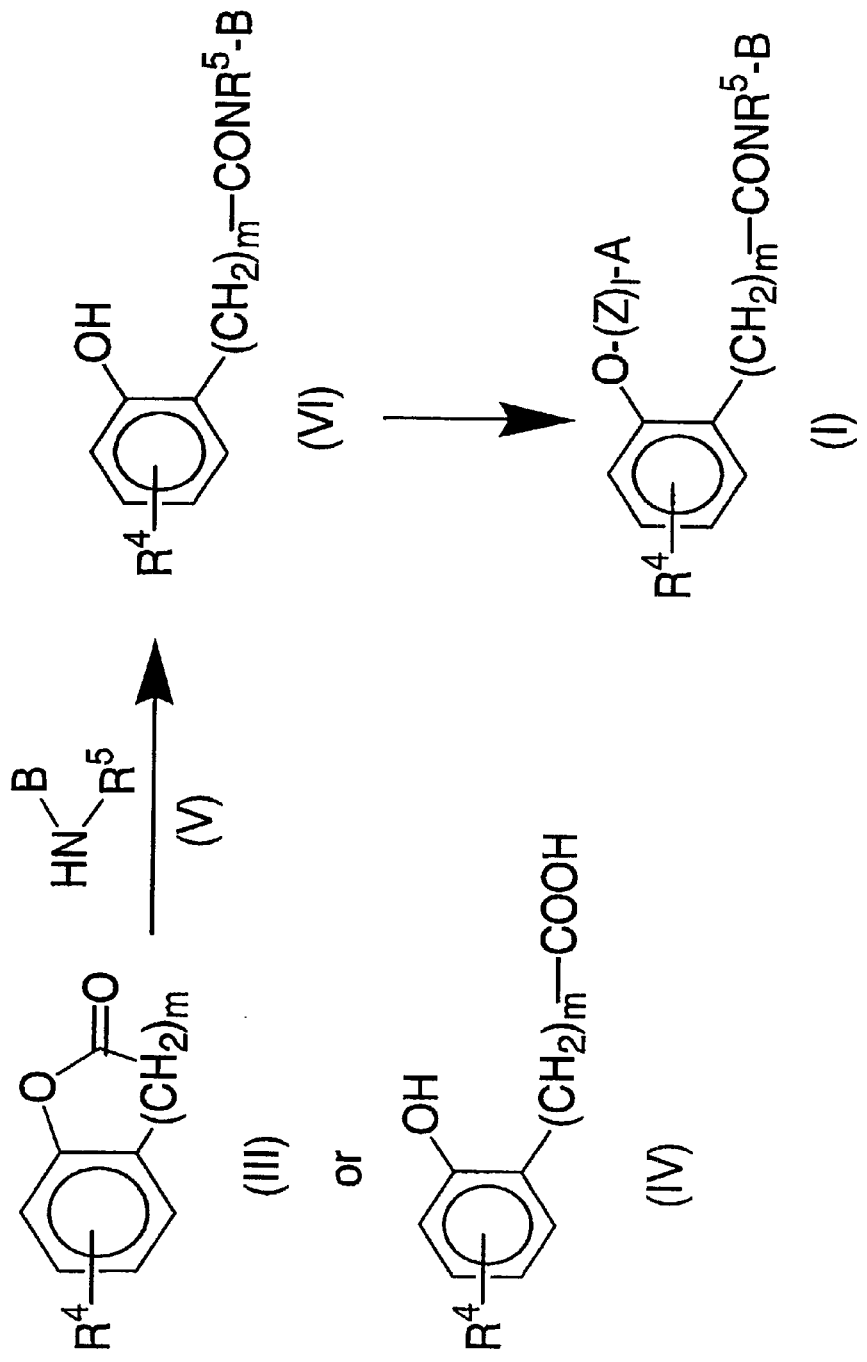
FIGS. 1–7 show examples of steps for manufacturing the (2-substituted oxyphenyl)alkanamide derivative in accordance with the present invention.

In the compound of the present invention, a hydrocarbon group of $C_{3-30}$ shown by $R^1$ refers to a straight or branched alkyl group having 3–30 carbon atoms, a straight or branched alkenyl group having 3–30 carbon atoms, a straight or branched alkynyl group having 3–30 carbon atoms, or an aromatic hydrocarbon group having 6–30 carbon atoms. Also, there may be one or two cycloalkyl rings having 3–8 carbon atoms at an optional position in $R^1$.

Examples of the above-mentioned straight alkyl group include propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tetracosyl, hexacosyl octacosyl and the like.

Examples of the above-mentioned branched alkyl group include isopropyl, isobutyl, tert-butyl, 2-methylpentyl, 4-isocapryl, 4-ethylpentyl, 6-methyldecyl, 9-methyldecyl, 6-ethylnonyl, 5-propyloctyl, 11-methyldodecyl, 12-methyltridecyl, 4-methyltetradecyl, 13-methyltridecyl, 14-ethylhexadecyl, 10-methyloctadecyl, 15-ethylheptadecyl, 10-methyldocosyl, 2-pentyloctadecyl, 22-methyltricosyl, 12-hexyloctadecyl, 6-methyltetracosyl, 24-methylheptacosyl, 2-decylhexadecyl, 2-nonyloctadecyl, 2-dodecyloctadecyl and the like.

Examples of the straight or branched alkenyl group having 3–30 carbon atoms and straight or branched alkynyl group having 3–30 carbon atoms include the alkenyl and alkynyl groups corresponding to the above-mentioned alkyl groups such as 2-butenyl, 3-octenyl, 4-decenyl, 7-dodecenyl, 9-octadodecenyl, 2-propynyl or 3-dodecynyl.

Examples of the aromatic hydrocarbon group having 6–30 carbon atoms include phenyl, 4-butylphenyl, 8-phenyloctyl, biphenylyl, naphtyl, and the like.

Also, examples of the hydrocarbon group having a cycloalkyl ring in $R^1$ include 12-cyclohexyldodecyl and the like.

Among these groups, $R^1$ is preferably a straight or branched alkyl group having 10–30 carbon atoms and, more preferably, a straight or branched alkyl group having 13–21 carbon atoms, and particularly preferably, octadecyl group. However, when Z=—CO— and l=1, $R^1$ is particularly preferably heptadecyl group. The hair growth effect tends to deteriorate in the case where the carbon number of $R^1$ is too small.

Each of $R^2$ and $R^3$, which may be identical or different from each other, can be a hydrogen, a lower alkyl or a benzyl group. Also, $—NR^2R^3$ may be a heterocycle having 3–7 members. Further, when B is $—(CH_2)n-NR^2R^3$ or when $-(Z)_1-A$ is $—CONR^6—(CH_2)n-NR^2R^3$, said $—CONR^5—(CH_2)n-NR^2R^3$ and said $—CONR^6—(CH_2)n-NR^2R^3$ may be said Group (II).

In $R^2$ and $R^3$, the lower alkyl group refers to a straight or branched alkyl group having 1–6 carbon atoms. Examples of the lower alkyl group include methyl, ethyl, propyl, butyl, isopropyl, isobutyl, 1-methylpropyl, tert-butyl, pentyl, 1ethylpropyl, isoamyl, hexyl and the like. For the lower alkyl group in $R^2$ and $R^3$, methyl or ethyl group is preferable. In the present invention, the definition of lower alkyl group is the same as mentioned above if there is no further description.

Also, the lower alkyl group in $R^2$ and $R^3$ may be substituted by one or two hydroxyl groups. Examples of such a hydroxy lower alkyl group include 2-hydroxyethyl group.

In $R^2$ and $R^3$, the benzyl group may be substituted by one or two of the same or different substituents, which can be selected from the group consisting of a halogen, a lower alkyl, a lower acyl, a nitro, a cyano, a lower alkoxycarbonyl, a lower alkylamino, a lower alkoxy and a lower acyloxy group. The definition of each substituent referred in here is explained as follows:

The halogen atom represents chlorine, bromine, iodine or fluorine.

The lower alkyl group is as mentioned above and, preferably, methyl or ethyl group.

The lower acyl group is a straight or branched acyl group having 2–7 carbon atoms. Examples of the lower acyl group include acetyl, propionyl, butyryl, isobutyryl, pivaloyl, benzoyl group and the like.

The lower alkoxycarbonyl group represents a carboxyl group whose hydrogen atom is substituted by a lower alkyl group. A preferable example of the lower alkoxycarbonyl group is methoxycarbonyl or ethoxycarbonyl group.

The lower alkylamino group represents an amino group whose hydrogen atom is substituted by one or two of the same or different lower alkyl groups. A preferable example of the lower alkylamino group is methylamino or dimethylamino group.

The lower alkoxy group represents a hydroxyl group whose hydrogen atom is substituted by a lower alkyl group. A preferable example of the lower alkoxy group is methoxy or ethoxy group.

The lower acyloxy group represents a hydroxyl group whose hydrogen atom is substituted by a lower acyl group, wherein said lower acyl group is as above-mentioned. A preferable example of the lower acyloxy group is acetoxy or propionyloxy group.

It is preferable that the benzyl group in $R^2$ and $R^3$ is unsubstituted.

The heterocycle having 3–7 members of $—NR^2R^3$ represents a saturated or unsaturated heterocycle containing the nitrogen atom to which $R^2$ and $R^3$ are bonded. In addition to the nitrogen atom, a hetero atom such as nitrogen, oxygen or sulfur atom may be contained in the heterocycle. Examples of the heterocycle include aziridine, azetidine, pyrrolidine, piperidine, homopiperidine, piperazine, morpholine, pyrrole, pyrazole, imidazole, thiomorpholine, thiazole and thiazolidine ring. Among these heterocycles, pyrrolidine, piperidine, piperazine or morpholine ring is preferable. The heterocycle may be substituted by one or two of the same or different substituents, which can be selected from the group consisting of a lower alkyl, a lower alkoxy and a nitro group. The lower alkyl group is preferably methyl or ethyl group. The lower alkoxy group is preferably methoxy or ethoxy group. The lower acyl group is preferably acetyl or propionyl group.

It is preferable that the heterocycle of —NR²R³ is unsubstituted.

In said Group (II), the ring Y is a saturated or unsaturated heterocycle having 6 or 7 members containing two nitrogen atoms and, preferably, a saturated heterocycle and, particularly preferably, piperazine ring. Also, there may be one or two of substituents such as oxo group on the heterocycle Y. R² of the Group (II) is a hydrogen atom, a lower alkyl group or a benzyl group and, preferably, lower alkyl or benzyl group. Preferable example of the lower alkyl group in R² is methyl group.

Group (II) include the following Groups (II-1) to (II-3):

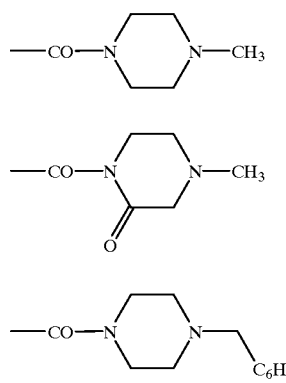

Among them, Group (II-1) is preferable.

As for R² and R³, it is preferable that: R² and R³ are lower alkyl groups; —NR²R³ is a heterocycle having 3–7 members; or R² and R³ form a part of said Group (II).

R⁴ can be a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group As for R⁴, the definitions for halogen, lower alkyl, lower acyl, lower alkoxycarbonyl, lower alkylamino, lower alkoxy and lower acyloxy groups are identical to those in R² and R³.

The lower alkylcarbamoyl group in R⁴ represents a carbamoyl group whose hydrogen atom is substituted by one or two of the same or different lower alkyl groups. A preferable example of the lower alkylcarbamoyl group in R⁴ is methylcarbamoyl or ethylcarbamoyl group.

The lower acylamino group in R⁴ represents an amino group whose hydrogen atom is substituted by one or two of the same or different lower acyl groups. The lower acyl group is as mentioned above. A preferable example of the lower acylamino group in R⁴ is acetylamino, propionylamino or benzoylamino group.

Among them, R⁴ is preferably a hydrogen atom.

R⁵ can be a hydrogen atom, a lower alkyl group, a lower acyl group or a lower alkylcarbamoyl group. Also, when B is —(CH₂)n-NR²R³, —CONR⁵—(CH₂)n-NR²R³ may be said Group (II). Preferably, R⁵ is a hydrogen atom or forms a part of Group (II).

R⁶ can be a hydrogen atom, a lower alkyl group, a lower acyl group or a lower alkylcarbamoyl group. Also, when —(Z)₁—A is —CONR⁶—(CH₂)n-NR²R³, said —CONR⁶—(CH₂)n-NR² R³ may be said Group (II). Preferably, R⁶ is a hydrogen atom or forms a part of Group (III).

As for R⁵ and R⁶, the definitions for lower alkyl and lower acyl groups are identical to those in R² and R³, and the definition for lower alkylcarbamoyl group is identical to that in R⁴.

Z is a divalent group expressed by —CO— or —CONR⁶—, and l is 0 or 1. When l is 1, Z is preferably —CONR⁶—.

m is 1 or 2 and, preferably, 2.

n is an integer of 0–5 and, preferably, an integer of 2–5 in view of stability and the like.

A preferable example of the present invention can be expressed by the following Formula (I-1):

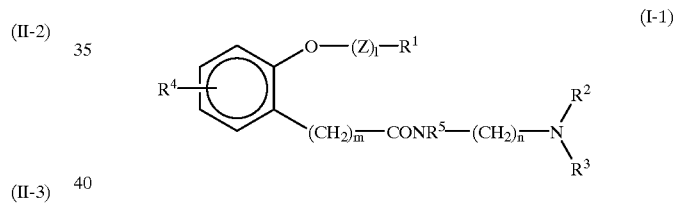

wherein R¹, R², R³, R⁴, R⁵, Z, l, m and n are as defined in said Formula (I).

In Compound (I-1), R⁵ is preferably a hydrogen atom. Also, it is preferable that R² and R³ are lower alkyl groups or —NR²R³ is a heterocycle of 3–7 members.

Also, a preferable example of Compound (I-1) can be expressed by the following Formula (I-2):

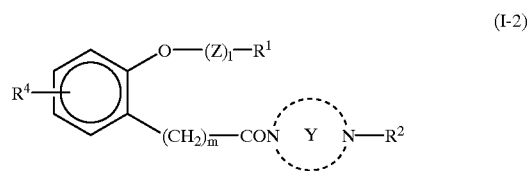

wherein Y is a heterocycle ring of 6 or 7 members containing two nitrogen atoms; R² is a hydrogen atom, a lower alkyl group or a benzyl group; and R¹, R², R⁴, Z, l and m are as defined in said Formula (I).

In Compound (I-2), it is preferable that ring Y is a piperazine ring and R² is a lower alkyl group.

Also, in Compound (I-2), it is preferable that ring Y is a piperazine ring and R² is a benzyl group.

Also, a preferable example of the present invention may be expressed by the following Formula (I-3):

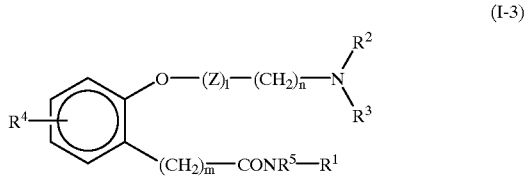

(I-3)

wherein $R^1$, $R^2$, $R^3$, $R^4$, $R^5$, Z, l, m and n are as defined in said Formula (I).

The Compound(I) of the present invention may have a asymmetric carbon in any of groups of $R^1$, $R^2$, $R^3$, $R^4$, $R^5$ and $R^6$. The present invention can include optical isomers based on the asymmetric carbon and the mixture thereof. Also, when there are the other isomers such as geometrical isomers or conformational isomers, the present invention can include them.

Compound (I) provided in the present invention can be manufactured by using known reactions. The representative synthetic examples will be shown in the following. Also, in the following manufacturing methods, $R^1$, $R^2$, $R^3$, $R^4$, $R^5$, $R^6$, A, B, Z, l, m and n are as shown in the definitions of Formula (I), unless otherwise indicated.

Compound (I) can be synthesized, for example, as shown in Reaction Formula A of FIG. 1. First, Compound (VI) is obtained by reacting a lactone (III) with an amine (V), and then Compound (VI) is subjected to a reaction according to Z and l, to give Compound (I).

The lactone (III) and amine(V) can be reacted in the absence or presence of a solvent. As a solvent, for example, a halogenated hydrocarbon such as dichloromethane or chloroform; an aromatic compound such as benzene, toluene, xylene or pyridine; an ether such as tetrahydrofuran or 1,4-dioxane; an amide such as N,N-dimethylformamide or N,N-dimethylacetamide; or a sulfoxide such as dimethylsulfoxide can be used. This reaction can be effected at the temperature within the range of room temperature to 150° C. and, preferably, at room temperature to 100° C. without a solvent.

Also, Compound (VI) can be synthesized from Compound (VI) and amine (V) by using a known amide-forming reaction.

In the following, an usual synthetic method of Compound (I) from Compound (VI) will be explained.

Compound (I-4)

(l=1, Z=—CONR$^6$—)

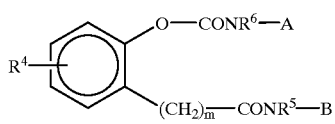

(I-4)

Figure 2:
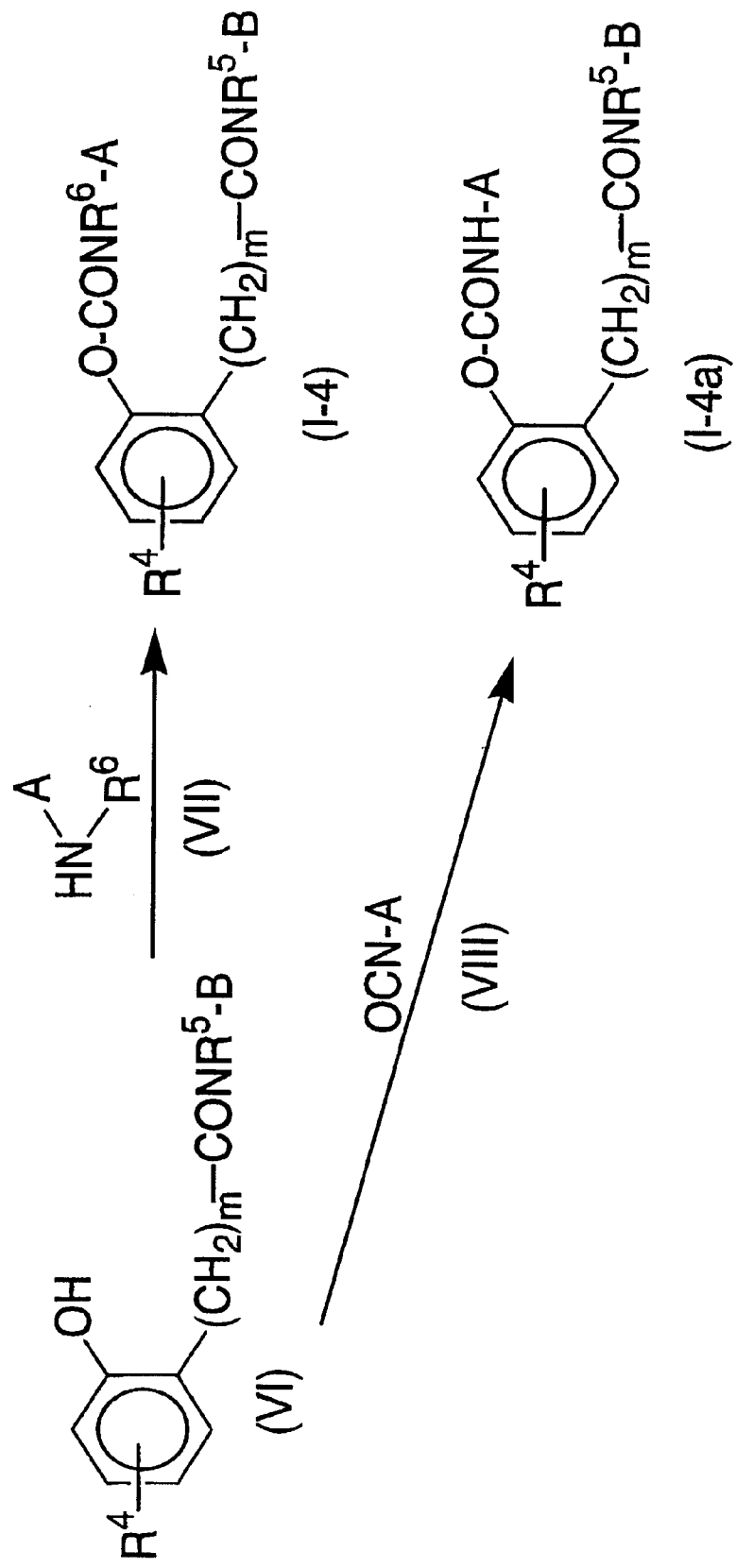

Compound (I-4), for example, can be synthesized by reacting Compound(VI) with an amine (VII) as shown in Reaction Formula B of FIG. 2. In this reaction, for example, using phenyl chlorocarbonate, phosgene, diphosgene, triphosgene, di-2-pyridylketone or the like, Compound (VI) is converted into its corresponding carbonate, and then the carbonate is reacted with the amine (VII). As an additive, for example, a base such as triethylamine, N,N-diisopropylethylamine, pyridine or sodium carbonate can be used. As a solvent, for example, a halogenated hydrocarbon such as dichloromethane or chloroform; an aromatic hydrocarbon such as benzene, toluene or xylene; or an ether such as tetrahydrofuran or 1,4-dioxane can be used. While the reaction temperature and reaction time may be changed according to the starting materials and the reagents used, the reaction is usually effected at a temperature within the range of −15° C. to the reflux temperature of the solvent. Specifically, for example, by using pyridine or N,N-diisopropylethylamine as an additive, Compound (VI) is reacted with phenyl chlorocarbonate or triphosgene in a solvent such as chloroform or dichloromethane at a temperature within the range of −15° C. to room temperature to give its corresponding carbonate. Then, the carbonate is reacted with the amine (VII) in the absence or presence of a solvent such as chloroform or dichloromethane at a temperature of room temperature to 100° C., thereby attaining the aimed object. Compound (I-4a) wherein $R^6$ of Compound (I-4) is a hydrogen atom can be also synthesized by addition reaction of Compound (VI) with an isocyanate (VIII). As an additive for this addition reaction, for example, an acid such as boron trifluoride etherate, hydrochloric acid, aluminum chloride, dialkyltin dichloride or dialkyltin acetate, or a base such as triethylamine, N,N-diisopropylethylamine, pyridine, N-methylmorpholine, N-methylpiperidine or sodium acetate can be used. As a solvent, for example, a halogenated hydrocarbon such as dichloromethane or chloroform; an aromatic hydrocarbon such as benzene, toluene or xylene; an ether such as tetrahydrofuran or 1,4-dioxane; or an amide such as N,N-dimethylformamide or N,N-dimethylacetamide can be used. While the reaction temperature and reaction time may be changed according to the starting materials and the reagents used, the reaction is usually effected at a temperature within the range of 0° C. to the reflux temperature of the solvent. Specifically, for example, by using triethylamine as an additive, Compound (VI) is reacted with the isocyanate (VIII) in a solvent such as dichloromethane at a temperature within the range of 0° C. to room temperature, thereby attaining the aimed object.

Such isocyanates can be commercially available or obtained by a reaction wherein the corresponding amine (VII) is reacted with phosgene, diphosgene, triphosgene or the like in the absence or presence of a base, or by a reaction wherein the corresponding carboxylic acid HO$_2$C—A is reacted with diphenylphosphoryl azide or the like in the presence of a base.

Compound (I-5)

(l=1, Z=—CO—)

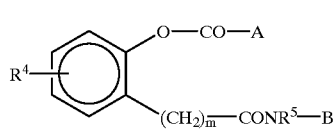

(I-5)

Figure 3:
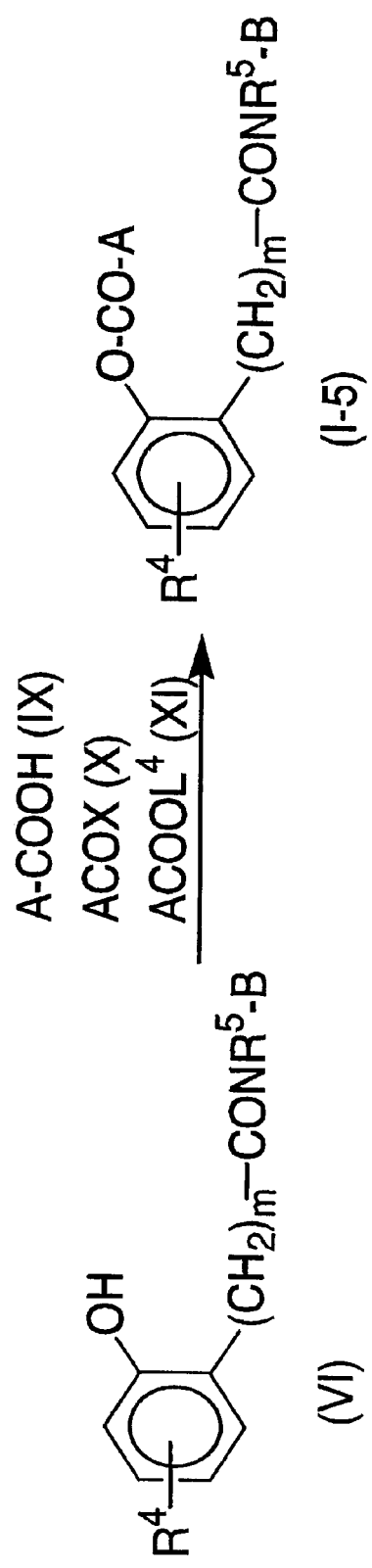

Compound (I-5) can be synthesized by introducing an acyl group —CO—A into a hydroxyl group of Compound (VI). For example, as shown in Reaction Formula C of FIG. 3, this reaction can be effected by a dehydrating condensation reaction of Compound (VI) with a carboxylic acid (IX), a reaction with an acid halide (X), an ester interchange reaction with an ester (XI) or the like.

As for the dehydrating condensation reaction with the carboxylic acid (IX), a method that the both compounds are directly reacted usually in the presence of an acidic catalyst, a method that the carboxylic acid (IX) is converted into its active ester and then the active ester is reacted with Compound (VI) or the like can be used. In the former method, as an acidic catalyst, a mineral acid such as hydrochloric acid, sulfuric acid or boric acid, an organic acid such as aromatic sulfonic acid, a Lewis acid such as boron trifluoride etherate, or the like can be used. As a solvent, an aromatic hydrocarbon such as benzene, toluene, or xylene; an ether such as tetrahydrofuran or 1,4-dioxane; an amide such as N,N-dimethylformamide or N,N-dimethylacetamide; a halogenated hydrocarbon such as dichloromethane or dichloroethane; or the like can be used. While the reaction temperature and reaction time may be changed according to the starting materials and the reagents used, the reaction is usually effected at a temperature within the range of 0° C. to the reflux temperature of the solvent. Specifically, for example, concentrated sulfuric acid is added to a solution of Compound (VI) and the carboxylic acid (IX) in dichloroethane and then the reaction is effected at a temperature within the range of room temperature to the reflux temperature of the solvent, thereby attaining the aimed object. Also, a mixture of Compound (VI), the carboxylic acid (IX) and boron trifluoride etherate is reacted at a temperature within the range of room temperature to the reflux temperature of the solvent, thereby attaining the aimed object.

In the latter method proceeding by way of the active ester of the carboxylic acid (IX), by using trifluoroacetic acid anhydride, N,N-dicyclohexylcarbodiimide (DCC) or the like, the carboxylic acid (IX) is converted into its corresponding active ester and then the active ester is reacted with Compound (VI). As a solvent, benzene, tetrahydrofuran, N,N-dimethylformamide, dichloromethane or the like can be used. While the reaction temperature and reaction time may be changed according to the starting materials and the reagents used, the reaction is usually effected at a temperature within the range of 0° C. to the reflux temperature of the solvent. Specifically, for example, trifluoroacetic acid anhydride is added to a solution of the carboxylic acid (IX) in benzene at a temperature within the range of 0° C. to room temperature to convert the carboxylic acid (IX) into its active ester and then the latter is reacted with Compound (VI), thereby attaining the aimed object.

The reaction with the acid halide (X) can be usually effected in the presence of a base. As a base, for example, an inorganic base such as sodium hydroxide or potassium hydroxide; or an organic base such as pyridine, dimethylaniline or triethylamine can be used. As a solvent, benzene, tetrahydrofuran, 1,4-dioxane, N,N-dimethylformamide or the like can be used. While the reaction temperature and reaction time may be changed according to the starting materials and the reagents used, the reaction is usually effected at a temperature within the range of 0° C. to the reflux temperature of the solvent. Specifically, for example, the acid halide (X) is added to a solution containing Compound (VI) and pyridine in dichloromethane and then the reaction is effected at a temperature within the range of 0° C. to room temperature, thereby attaining the aimed object. Also, sodium hydroxide aqueous solution is dropwise added to a mixture of Compound (VI) and acid halide (X), thereby attaining the aimed object. X in the Reaction Formula represents a halogen atom. The definition of X throughout the rest of this specification remains the same.

In the ester interchange reaction with the ester (XI), as a catalyst, an acid such as sulfuric acid or p-toluenesulfonic acid, or a base such as potassium alkoxide or titanium (IV) alkoxide can be used. The reaction can be effected in the absence or presence of a solvent. In this reaction, it is preferable that either Compound (VI) or the ester (XI) is used excessively, or that an alcohol $L^4OH$ produced during the reaction is removed from the reaction system in view of the reaction property. As a solvent, benzene, toluene, tetrahydrofuran, 1,4-dioxane, N,N-dimethylformamide, dichloromethane or the like can be used. While the reaction temperature and reaction time may be changed according to the starting materials and the reagents used, the reaction is usually effected at a temperature within the range of 0° C. to 200° C. and, preferably, room temperature to the reflux temperature of the solvent. Specifically, for example, titanium(IV) alkoxide is added to a solution containing Compound (VI) and the ester (XI) in benzene and then the reaction is effected at a temperature within the range of room temperature to the reflux temperature of the solvent, thereby attaining the aimed object. As for $L^4$ of the Reaction Formula, any of groups can be used if they form esters usually used for this ester interchange reaction. Examples of $L^4$ include an alkyl group such as methyl or ethyl group. The definition of $L^4$ throughout the rest of this specification remains the same.

Compound (I-6)

(1=0)

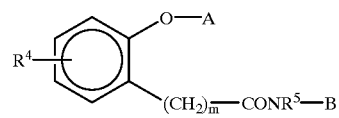

(I-6)

Figure 4:
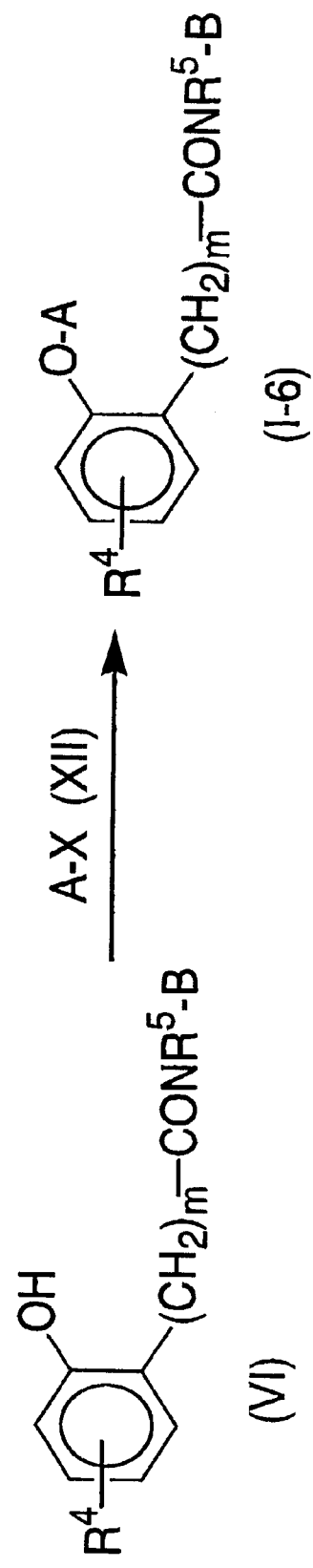

Compound (I-6) can be synthesized by reacting Compound (VI) with halide (XII) as shown in Reaction Formula D of FIG. 4.

In this reaction, Compound (VI) is converted into its corresponding alkoxide by using metallic sodium, sodium hydride or the like and then the alkoxide is reacted with the halide (XII). Also, Compound (VI) can be reacted with halide (XII) in the presence of a base directly. As a base, sodium amide, potassium carbonate, sodium hydroxide, barium oxide, silver oxide or the like can be used. As a solvent, an aromatic hydrocarbon such as benzene, toluene, or xylene; an ether such as tetrahydrofuran or 1,4-dioxane; an amide such as N,N-dimethylformamide, N,N-dimethylacetamide or hexamethylphosphorylamide; acetonitrile; dimethyl sulfoxide; or the like can be used. While the reaction temperature and reaction time may be changed according to the starting materials and the reagents used, the reaction is usually effected at a temperature within the range of 0° C. to the reflux temperature of the solvent. Specifically, for example, Compound (VI) is reacted with the halide (XII) in acetone in the presence of potassium carbonate at a temperature within the range of room temperature to the reflux temperature of the solvent, thereby attaining the aimed object.

In addition, Compound (I-6) can be synthesized by a substitution reaction of Compound (VI) with a suitable ester compound such as sulfonate, phosphate or orthate, or by addition reaction of Compound (VI) with a suitable alkene.

Figure 5:
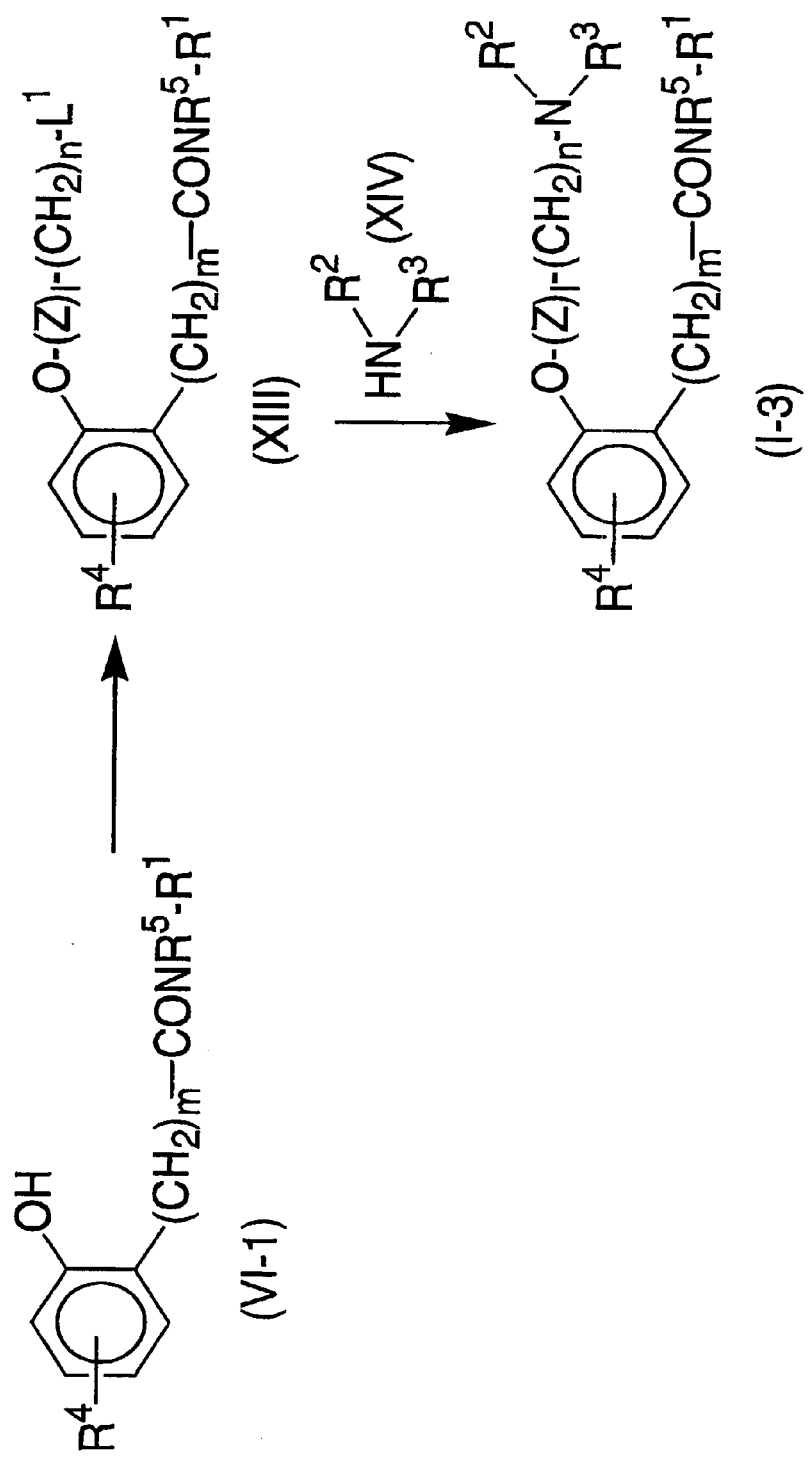

Although the above is a usual synthetic method, for introducing the group $—(CH_2)n—NR^2R^3$ into the structure of the compound, a method wherein a group $—(CH_2)n-L^1$ is introduced and then $—L^1$ is substituted with $—NR^2R^3$ can be used. For example, as shown in Reaction Formula E of FIG. 5, Compound (XIII) is synthesized from Compound (VI-1) and then Compound (XIII) is reacted with an amine (XIV) to give Compound (I-3). $L^1$ is an atom or a group which can be easily substituted with nitrogen atom. Examples of $L^1$ include a halogen, tosyloxy or mesyloxy group.

The reaction at the first step of Reaction Formula E can be effected according to the methods of Reaction Formulae B to D.

The reaction at the second step of Reaction Formula E can be effected in the presence of a base. As a base, for example, an inorganic base such as potassium carbonate, potassium hydroxide, sodium hydroxide or sodium hydride, or an organic base such as triethylamine or pyridine can be used. As a solvent, toluene, ether, tetrahydrofuran, acetone, N,N-dimethylformamide or the like can be used. Specifically, for example, by using potassium carbonate as a base, the reaction is effected in a solvent such as acetone or N,N-dimethylformamide at the temperature with the range of room temperature to the reflux temperature of the solvent, thereby attaining the aimed object.

The reactions in this Reaction Formula E can also be applied for synthesis of Compound (I-1).

Figure 6:
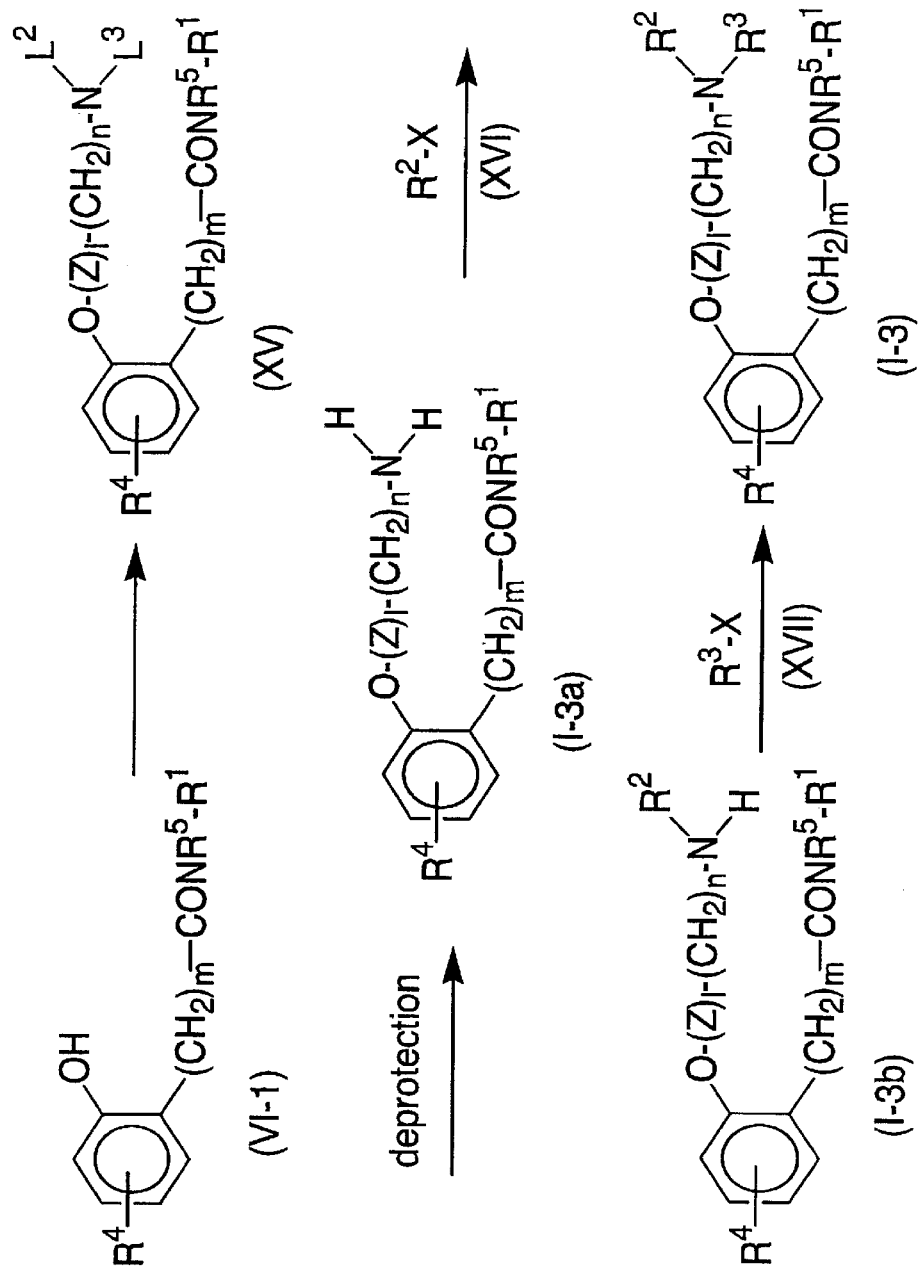

Also, as an another method for introducing group —($CH_2$)n-$NR^2R^3$ into the structure of the compound, a method that —($CH_2$)—$NL^2L^3$ is introduced and converted into —($CH_2$)—$NH_2$ by deprotection, and then $R^2$ and $R^3$ are introduced thereinto can be used. For example, as shown in Reaction Formula F of FIG. 6, Compound (XV) is synthesized from Compound (VI-1) and then deprotected to give Compound (I-3a) wherein $R^2$ and $R^3$ are H.

Further, Compound (I-3b) can be obtained by reacting Compound (I-3a) with about one equivalent amount of a halide (XVI) in the presence of a base. Furthermore, Compound (1–3) can be obtained by reacting Compound (I-3b) with a halide (XVII).

In Reaction Formula F, either $L^2$ or $L^3$ can be an amino protecting group such as an urethane type protecting group (e.g., tert-butoxycarbonyl, benzyloxycarbonyl or 9-fluorenylmethyloxycarbonyl group), a sulfonyl type protecting group (e.g., 2-(trimethylsilyl)ethanesulfonyl group), a sulfenyl type protecting group (e.g., 2,2,2-trifluoro-1,1-diphenylethanesulfenyl group), or an alkyl type protecting group (e.g., benzyl, trityl or 9-phenylfluorenyl group), while the other can be a hydrogen atom. Also, $L^2$ and $L^3$ together can form a phthalimide type amino protecting group. Further, other protecting group can be used unless it is adverse to the object of this Reaction Formula.

The first step of Reaction Formula F can be effected according to Reaction Formulae B to D.

For the deprotection at the second step of Reaction Formula F, various kind of known methods can be used according to the type of amino protecting group $L^2$ and $L^3$. For example, in the case where $L^2$ is a benzyloxycarbonyl and $L^3$ is a hydrogen atom, by using palladium-carbon as a catalyst, the reaction is effected in a solvent such as ethanol or ethyl acetate in a hydrogen atmosphere at a temperature within the range of room temperature to the reflux temperature of the solvent, thereby attaining the aimed object. Also, in the case where $L^2$ and $L^3$ together form a phthalimide type amino protecting group, by using hydrazine as a deprotection agent, the reaction is effected in ethanol at a temperature within the range of room temperature to the reflux temperature of the solvent, thereby attaining the aimed object.

In the reactions at the third and forth steps of Reaction Formula F, when $R^2$ and $R^3$ are lower alkyl or benzyl groups, an inorganic base such as potassium carbonate, potassium hydroxide, sodium hydroxide or sodium hydride; or an organic base such as triethylamine or pyridine can be used as a base. Specifically, for example, by using potassium carbonate as a base, the reaction is effected in a solvent such as acetone or N,N-dimethylformamide at a temperature within the range of room temperature to the reflux temperature of the solvent, thereby attaining the aimed object.

In a similar manner to the above, by reacting Compound (I-3a) with about twice equivalent amount of halide (XVI) in the presence of a base, a compound wherein $R^2$ and $R^3$ of Compound (I-3) are the same can be obtained. Also, by reacting Compound (I-3a) with a suitable dihalogenated compound, a compound wherein —$NR^2R^3$ of Compound (I-3) is a heterocycle having 3–7 members can be obtained.

The reactions in this Reaction Formula F can also be applied for synthesis of Compound (I-1).

Figure 7:
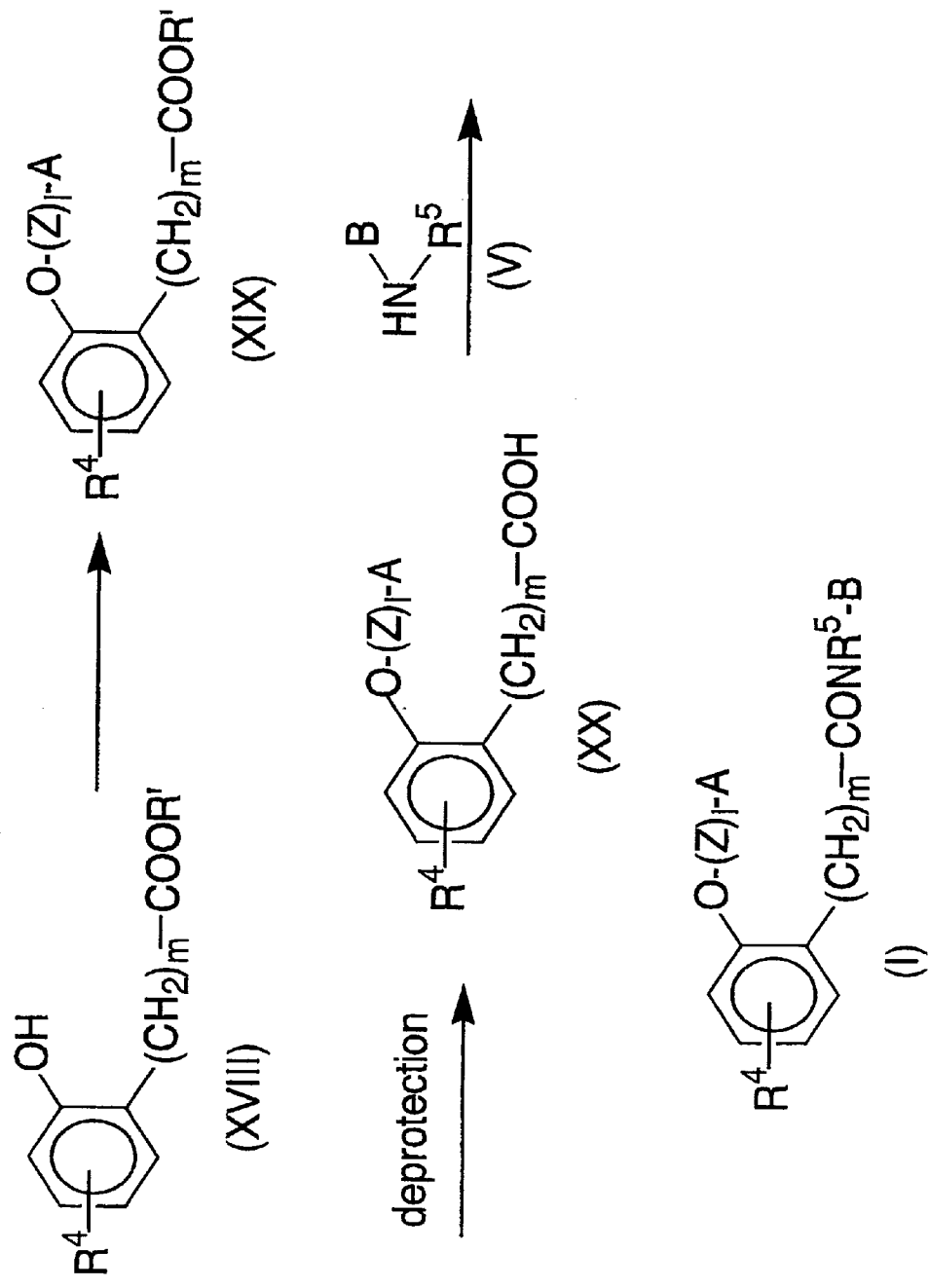

Also, Compound (I) can be synthesized as shown in Reaction Formula G of FIG. 7. Namely, Compound (XIX) synthesized from Compound (XVIII) is deprotected and then reacted with the amine (V) to give Compound (I). In Reaction Formula G, R' is a carboxyl-protecting group such as tert-butyl, benzyl, methoxymethyl or trityl group. Also, other carboxyl-protecting group can be used unless it is adverse to the object of this reaction.

For the reaction at the first step of Reaction Formula G, reactions appropriately selected from Reaction Formulae B to F can be used. For the deprotecting reaction at the second step, various kind of known methods can be used according to the type of carboxyl-protecting group R'. For example, in the case where R' is a tert-butyl group, the reaction is effected in trifluoroacetic acid at room temperature. Also, in the case where R' is a benzyl group, for example, by using palladium-carbon as a catalyst, the reaction is effected in a solvent such as ethanol or ethyl acetate in a hydrogen gas atmosphere at a temperature within the range of room temperature to the reflux temperature of the solvent, thereby attaining the aimed object. The reaction at the third step can be effected by known amide-forming reaction.

Although a compound wherein $R^5$ or $R^6$ in Compound (I) is a lower alkyl, a lower acyl or a lower alkylcarbamoyl group can be synthesized according to the above-mentioned Reaction Formulae, it can be also synthesized as follows: first, a compound wherein $R^5$ or $R^6$ of Compound (I) is a hydrogen atom is synthesized according to the above-mentioned Reaction Formulae; and then the resulting compound is reacted with a suitable halide such as alkyl halide, acyl halide or alkylcarbamoyl halide in the absence or presence of a base.

Among the starting materials used in the foregoing Reaction Formulae, what are not described above are commercially available or can be easily synthesized from a suitable starting material by using known methods.

The (2-substituted oxyphenyl)alkanamide derivative (I) provided in the present invention can be changed to an acid-added salt if necessary. Examples of the acid-added salt include salt with an inorganic acid such as hydrochloric acid, hydrobromic acid, sulfuric acid or phosphoric acid and salts with an organic acid such as acetic acid, propionic acid, citric acid, lactic acid, oxalic acid, maleic acid, fumaric acid, succinic acid, tartaric acid or methanesulfonic acid. These salts can be easily manufactured by common methods.

The (2-substituted oxyphenyl)alkanamide derivatives in accordance with the present invention, which mechanism of action has not been made clear, have an excellent hair growth and regrowth promoting effect. Accordingly, by applying the compound on skin of mammals such as human scalp, care, improvement, or prevention of hair loss can be expected.

The (2-substituted oxyphenyl)alkanamide derivative of the present invention can apply to pathological alopecia such as alopecia areata, alopecia pityrodes or alopecia seborrheica in addition to thin hair or hair loss what is called male pattern baldness or androgenic alopecia. The dosage of the (2-substituted oxyphenyl)alkanamide derivative in accordance with the present invention must be determined suitably according to sex, age and degree of symptom in hair loss or thin hair. Usually 0.01–20 mg/cm$^2$ is applied on scalp per day for an adult in a single dose or several doses.

When the (2-substituted oxyphenyl)alkanamide derivative of the present invention is used as a drug, quasi-drug or cosmetic for hair growth and regrowth promoting and prevention of hair loss, its pharmaceutical form can be selected voluntarily as long as the effects of the present invention can be exhibited. Examples of the pharmaceutical form include tonic, lotion, milky lotion, cream, ointment, gel, spray, mousse and the like.

In addition to the (2-substituted oxyphenyl)alkanamide derivative in accordance with the present invention, various pharmaceutically acceptable ingredients, which are generally compounded to hair growth promoting composition in the field of drug, quasi-drug and cosmetic, can be compounded to these preparations.

For example, as a drug having a blood flow promoting action, swertia herb extract, vitamin E and derivatives thereof, nicotinates such as benzyl nicotinate, and the like can be used. Examples of drugs which promote blood circulation by topical stimulation include capsicum tincture, cantharides tincture, camphor and vanillic acid nonylamide. Examples of drugs having hair follicle activating action include hinokitiol, placental extract, photosensitizing dye, pantothenic acid and derivatives thereof. Examples of drugs having antiandrogen action include a hormone such as estradiol or estrone. Examples of drugs having antiseborrheic action include sulfur, thioxolone and vitamin B6.

In addition, salicylic acid, resorcine and the like which has corneocycle desquamating and antibacterial action can be compounded therein so as to prevent the generation of dandruff. Also, glycyrrhizic acid and derivatives thereof, menthol, and the like can be compounded therein so as to prevent inflammation of scalp. Further, an amino acid such as serine, methionine or arginine, a vitamin such as biotin, extracts of crude drugs and the like can be compounded therein in order to supplement nutrition for hair follicle and activate enzyme activity.

Also, extracts from plants such as althea, coix, peppermint, leaf base, capsicum, aloe, lycium, mugwort, oryza, seashore vitex, rosmarinus officinalis, drynaria, cytisus scoparius, gentiana, salviae miltiorrhizeae radix, sponge gourd, platycodon, pinus, sophora root, Japanese angelica root, safflower, Japanese barberry, areca, eucalyptus, prunella spike, akebia stem, achyranthes root, bupleurum root, tea, licorice, hop, Chrysanthemum, senega, sesame, cnidium rhizome, cashew, pueraria root, rosae rugosae flos, saffron, rosemary, rehmannia root, or mallow can be compounded.

Also, a vasodilator such as alkoxycarbonylpyridine N-oxide, carpronium chloride or acetylcholine derivative; a cutaneous hyperfunctioning agent such as cephalanthin; an antibacterial agent such as hexachlorophene, benzalkonium chloride, cetylpyridinium chloride, undecylenic acid, trichlorocarbanilide or bithionol; zinc and its derivatives; lactic acid and its alkyl ester; an organic acid such as citric acid; a protease inhibitor such as tranexamic acid; and the like can be compounded.

Further, an alcohol such as ethanol or isopropanol; a polyvalent alcohol such as glycerin, propylene glycol or polyethylene glycol; an oily ingredient such as higher fatty acids, higher alcohols, hydrocarbons, natural oils and fats, ester oils or silicone oils; surfactants; perfumes; chelating agents; humectants such as 1,3-butyleneglycol, hyaluronic acid and its derivatives, maltitol, soluble collagen or sodium lactate; thickening agents such as quince mucilage, carboxyvinylpolymer or xanthan gum; antioxidants; ultraviolet absorbers: coloring agents; water; stabilizers; and the like, which are generally compounded in hair growth composition, can be compounded within the range provided that the effects of the present invention are not spoiled.

EXAMPLES

In the following, the present invention will be explained by using specific examples. However, the present invention should not be restricted thereto.

Hair Regrowth Test (1) Test Method

By using C3H/HeNCrj mice, whose hair cycle was in resting stage, the experiment was performed according to the method of Ogawa et. al. (Normal and Abnormal Epidermal Differentiation, Edited by M. Seiji and I. A. Bernstein, Pages 159–170, 1982, Todai Shuppan). 10 mice were used in a group and the mice's hair within the area of 3×4 cm of the regions of back was shaved by a clipper and a shaver. 0.1 ml of ethanol (negative contrast) or ethanol solution of the tested compound (0.1 w/v %) was applied on the shaved portion once a day. For hair regrowth effect of the tested compound, the hair regrowth area of mice's region of back was measured and ratio of the hair regrowth area with respect to the shaved area was evaluated as hair regrowth area rate (%).

(2) Result

The average of hair regrowth area rate after each of the following tested compound was applied is shown in TABLE 1.

Compound 1:
2-[3-[[3-(Dimethylamino)propyl]amino]-3-oxopropyl] phenyl N-octadecylcarbamate
Compound 2:
2-[3-[[3-(Dimethylamino)propyl]amino]-3-oxopropyl] phenyl N-octadecylcarbamate hydrochloride
Compound 3:
2-[3-(4-Methylpiperazino)-3-oxopropyl]phenyl N-octadecylcarbamate
Compound 4:
2-[3-(4-Methylpiperazino)-3-oxopropyl]phenyl N-octadecylcarbamate hydrochloride
Compound 5:
2-{3-[(3-Morpholinopropyl)amino]-3-oxopropyl}phenyl N-octadecylcarbamate
Compound 6:
2-{3-[(3-Morpholinopropyl)amino]-3-oxopropyl}phenyl N-octadecylcarbamate hydrochloride
Compound 8:
N-[3-(Dimethylamino)propyl]-3-[2-(octadecyloxy) phenyl]propanamide hydrochloride
Compound 10:
N-(3-Morpholinopropyl)-3-[2-(octadecyloxy)phenyl] propanamide hydrochloride
Compound 12:
1-(4-Methylpiperazino)-3-[2-(octadecyloxy)phenyl]-1-propanone hydrochloride

TABLE 1

| Compound | Days of Application (days) | Hair Regrowth Area Rate (%) |
|---|---|---|
| Ethanol (negative contrast) | 24 | 0 |
| Compound 1 | 23 | 69 |
| Compound 2 | 23 | 10 |
| Compound 3 | 24 | 100 |
| Compound 4 | 24 | 100 |
| Compound 5 | 24 | 16 |
| Compound 6 | 24 | 17 |
| Compound 8 | 24 | 100 |
| Compound 10 | 24 | 38 |
| Compound 12 | 24 | 38 |

As is clear from TABLE 1, (2-substituted oxyphenyl) alkanamide derivatives and their pharmacologically acceptable salts in accordance with the present invention show excellent hair regrowth and growth promoting effects.

In the following, examples of compounds and compositions in accordance with the present invention will be explained.

Example 1

2-[3-[[3-(Dimethylamino)propyl]amino]-3-oxopropyl]phenyl N-octadecylcarbamate (Compound 1)

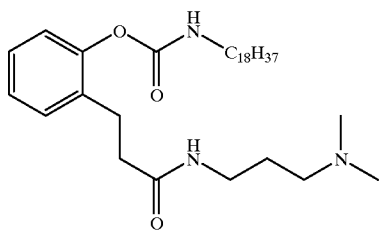

(1) N-[3-(Dimethylamino)propyl]-3-(2-hydroxyphenyl) propanamide

N,N-Dimethyl-1,3-propanediamine (1.40 g) was added to 3,4-dihydrocoumarine (2.01 g) and stirred for 0.5 hour at 70° C., thereby yielding the entitled compound (3.60 g) as white solid.

$^1$H-NMR (CDCl$_3$) δ:1.59 (2H, quintet, J=6.4 Hz), 2.18 (6H, s), 2.31 (2H, t, J=6.4 Hz), 2.56 (2H, t, J=5.9 Hz), 2.91 (2H, t, J=5.9 Hz), 3.31 (2H, q, J=6.4 Hz), 6.81 (1H, td, J=7.3, 1.5 Hz), 6.89 (1H, dd, J=7.3, 1.5 Hz), 7.04 (1H, dd, J=7.3, 1.5 Hz), 7.10 (1H, td, J=7.3, 1.5 Hz), 7.33 (1H, brs).

(2) 2-[3-[[3-(Dimethylamino)propyl]amino]-3-oxopropyl] phenyl N-octadecylcarbamate Triethylamine (0.62 ml) and octadecyl isocyanate (1.38 ml) were added to a solution containing N-[3-(dimethylamino)propyl]-3-(2-hydroxyphenyl)propanamide (1.00 g) in methylene chloride (10 ml). After being stirred for 3.5 hours at room temperature, the reaction mixture was diluted with chloroform, washed with saturated sodium hydrogencarbonate aqueous solution and water successively, dried over sodium sulfate anhydride, and concentrated. The residue was purified by silica gel column chromatography (silica gel 50 g, chloroform: methanol=30: 1 to 10: 1), thereby yielding the entitled compound (1.93 g) as white solid.

$^1$H-NMR (CDCl$_3$) δ: 0.88 (3H, t, J=6.8 Hz), 1.2–1.4 (30H, m), 1.49 (2H, quintet, J=6.4 Hz), 1.58 (2H, m), 2.14 (6H, s), 2.20 (2H, t, J=6.4 Hz), 2.38 (2H, t, J=7.3 Hz), 2.91 (2H, t, J=7.3 Hz), 3.20 (2H, q, J=6.4 Hz), 3.26 (2H, q, J=6.8 Hz), 5.33 (1H, brt), 6.65 (1H, brt), 7.08 (1H, d, J=7.8 Hz), 7.12 (1H, t, J=7.8 Hz), 7.20 (1H, d, J=7.8 Hz), 7.21 (1H, t, J=7.8 Hz).

Example 2

2-[3-[[3-(Dimethylamino)propyl]amino]-3-oxopropyl]phenyl N-octadecylcarbamate hydrochloride (Compound 2)

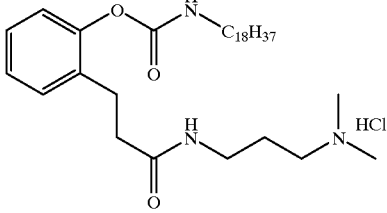

4N Hydrochloric acid/ethyl acetate solution (0.10 ml) was added to a solution containing 2-[3-[[3-(dimethylamino) propyl]amino]-3-oxopropyl]phenyl N-octadecylcarbamate (0.20 g) in ethyl acetate (4 ml) while being cooled with ice. After being stirred for 20 minutes, the reaction mixture was concentrated. The residue was recrystallized with the mixed solution of ethyl acetate-ethanol, thereby yielding the entitled compound (0.15 g) as white solid.

$^1$H-NMR (CDCl$_3$) δ: 0.88 (3H, t, J=6.8 Hz), 1.2–1.4 (30H, m), 1.61 (2H, m) 1.91 (2H, m), 2.54 (2H, t, J=7.3 Hz), 2.69 (6H, s), 2.78 (2H, t, J=6.8 Hz), 2.94 (2H, t, J=7.3 Hz), 3.23–3.32 (4H, m), 6.06 (1H, t, J=5.6 Hz), 7.12 (2H, m), 7.21 (2H, m), 7.25 (1H,brs), 11.75 (1H, brs).

Example 3

2-[3-(4-Methylpiperazino)-3-oxopropyl]phenyl N-octadecylcarbamate (Compound 3)

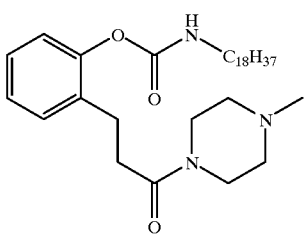

(1) 3-(2-Hydroxyphenyl)-1-(4-methylpiperazino)-1-propanone

N-Methylpiperazine (1.23 g) was added to 3,4-dihydrocoumarine (1.80 g) and stirred for 2 hours at 80° C., thereby yielding the entitled compound (3.12 g) as pale brown solid.

$^1$H-NMR (CDCl$_3$) δ: 2.28 (3H, s), 2.34 (4H, t, J=5.1 Hz), 2.71 (2H, t, J=5.6 Hz),2.95 (2H, t, J=5.6 Hz), 3.43 (2H, t, J=5.1 Hz), 3.63 (2H, t, J=5.1 Hz), 6.82 (1H, td, J=7.3, 1.0 Hz),6.91 (1H, dd, J=7.3, 1.0 Hz), 7.05 (1H, dd, J=7.3, 1.0 Hz), 7.11 (1H, td, J=7.3, 1.0 Hz), 9.54 (1H, brs).

(2) 2-[3-(4-Methylpiperazino)-3-oxopropyl]phenyl N-octadecylcarbamate

Triethylamine (0.62 ml) and octadecyl isocyanate (1.40 ml) were added to a solution containing 3-(2-hydroxyphenyl)-1-(4-methylpiperazino)-1-propanone (1.00 g) in methylene chloride (10 ml) and stirred for 4 hours at room temperature. The insoluble matters were filtrated out and washed with chloroform. The filtrate and washings were combined and the mixture was washed with saturated sodium hydrogencarbonate aqueous solution and brine successively, dried over sodium sulfate anhydride, and concentrated. The residue was purified by silica gel column chromatography (silica gel 50 g, chloroform:methanol= 50:1), thereby yielding the entitled compound (2.05 g) as white solid.

$^1$H-NMR (CDCl$_3$) δ: 0.88 (3H, t, J=6.8 Hz), 1.2–1.4 (30H, m), 1.57 (2H, m), 2.21 (2H), J=4.9 Hz), 2.26 (3H, s), 2.33 (2H, t, J=4.9 Hz), 2.57 (2H, t, J=7.3 Hz), 2.93 (2H, t, J=7.3 Hz), 3.25 (2H, q, J=6.8 Hz), 3.36 (2H, t, J=4.9 Hz), 3.63 (2H, t, J=4.9 Hz), 5.17 (1H, brt), 7.10–7.15 (2H, m), 7.19–7.24 (2H, m).

Example 4

2-[3-(4-Methylpiperazino)-3-oxopropyl]phenyl N-octadecylcarbamate hydrochloride (Compound 4)

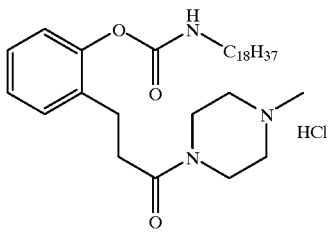

4N Hydrochloric acid/ethyl acetate solution (0.11 ml) was added to a solution containing 2-[3-(4-methylpiperazino)-3-oxopropyl]phenyl N-octadecylcarbamate (0.20 g) in ethyl acetate (2 ml) while being cooled with ice. After being stirred for 20 minutes, the reaction mixture was concentrated. The residue was recrystallized with the mixed solution of ethyl acetate-ethanol, thereby yielding the entitled compound (0.19 g) as white solid.

$^1$H-NMR (CDCl$_3$) δ: 0.88 (3H, t, J=6.8 Hz), 1.2–1.4 (30H, m), 1.59 (2H, m), 2.50 (2H, m), 2.57 (3H, s), 2.71 (1H, m), 2.98 (1H, m), 3.03 (2H, m), 3.25 (2H, q, J=6.8 Hz), 3.2–3.4 (3H, m), 3.78 (2H, m), 4.69 (1H, m), 5.26 (1H, brt), 7.11 (1H, d, J=8.3 Hz), 7.15 (1H, t, J=7.3 Hz), 7.25 (2H, m), 12.90 (1H, brs).

Example 5

2-{3-[(3-Morpholinopropyl)amino]-3-oxopropyl}phenyl N-octadecylcarbamate (Compound 5)

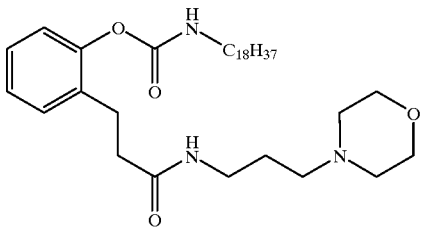

(1) 3-(2-Hydroxyphenyl)-N-(3-morpholinopropyl)propanamide

N-(3-Aminopropyl)morpholine (1.77 g) was added to 3,4-dihydrocoumarine (1.81 g) and stirred for 1 hours at 70° C., thereby yielding the entitled compound (4.16 g) as pale yellow syrup.

$^1$H-NMR (CDCl$_3$) δ: 1.60 (2H, quintet, J=6.4 Hz), 2.39 (4H, brt), 2.40 (2H, t, J=6.4 Hz), 2.56 (2H, t, J=5.9 Hz), 2.93 (2H, t, J=5.9 Hz), 3.34 (2H, q, J=6.4 Hz), 3.67 (4H, t, J=4.6 Hz), 6.82 (1H, td, J=7.8, 1.0 Hz), 6.90 (1H, dd, J=7.8, 1.0 Hz), 7.04 (1H, dd, J=7.8, 1.0 Hz), 7.11 (1H, td, J=7.8, 1.0 Hz), 7.31 (1H, brt), 8.95 (1H, brs).

(2) 2-[3-[(3-Morpholinopropyl)amino]-3-oxopropyl·phenyl N-octadecylcarbamate

Triethylamine (0.56 ml) and octadecyl isocyanate (1.26 ml) were added to a solution containing 3-(2-hydroxyphenyl)-N-(3-morpholinopropyl)propanamide (1.05 g) in methylene chloride (11 ml) and stirred for 3 hours at room temperature. The insoluble matters were filtrated out and washed with chloroform. The filtrate and washings were combined and the mixture was washed with saturated sodium hydrogencarbonate aqueous solution and water successively, dried over sodium sulfate anhydride, and concentrated. The residue was purified by silica gel column chromatography (silica gel 50 g, chloroform: methanol=60:1 to 50:1), thereby yielding the entitled compound (1.78 g) as white solid.

$^1$H-NMR (CDCl$_3$) δ: 0.88 (3H, t, J=6.8 Hz), 1.2–1.4 (30H, m), 1.49 (2H, quintet, J=6.4 Hz), 1.58 (2H, quintet, J=7.3 Hz), 2.25 (2H, t, J=6.4 Hz), 2.33 (4H, brt), 2.37 (2H, t, J=7.1 Hz), 2.93 (2H, t, J=7.1 Hz), 3.20 (2H, q, J=6.4 Hz), 3.26 (2H, q, J=7.3 Hz), 3.62 (4H, t, J=4.6 Hz), 5.30 (1H, brt), 6.62 (1H, brt), 7.09 (1H, d, J=7.3 Hz), 7.11 (1H, t, J=7.3 Hz), 7.20 (1H, d, J=7.3 Hz), 7.23 (1H, t, J=7.3 Hz).

Example 6

2-{3-[(3-Morpholinopropyl)amino]-3-oxopropyl}phenyl N-octadecylcarbamate hydrochloride (Compound 6)

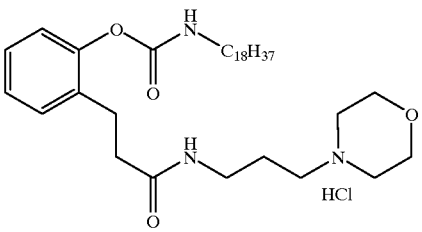

4N Hydrochloric acid/ethyl acetate solution (0.10 ml) was added to a solution containing 2-3-[(3-morpholinopropyl) amino]-3-oxopropyl phenyl N-octadecylcarbamate (0.20 g) in ethyl acetate (2 ml) while being cooled with ice. After being stirred for 30 minutes at room temperature, the reaction mixture was concentrated. The residue was recrystallized with ethyl acetate, thereby yielding the entitled compound (0.19 g) as white solid.

$^1$H-NMR (CDCl$_3$) δ: 0.88 (3H, t, J=6.8 Hz), 1.2–1.4 (30H, m), 1.60 (2H, quintet, J=7.3 Hz), 1.95 (2H, quintet, J=5.9 Hz), 2.53 (2H, t, J=7.3 Hz), 2.75 (4H, m), 2.94 (2H, t, J=5.9 Hz), 3.23–3.32 (6H, m), 3.94 (2H, d, J=12.2 Hz), 4.23 (2H, t, J=12.2 Hz), 5.97 (1H, t, J=5.9 Hz), 7.11 (2H, m), 7.19–7.25 (3H, m), 12.24 (1H, brs).

Example 7

N-[3-(Dimethylamino)propyl]-3-[2-(octadecyloxy)phenyl]propanamide (Compound 7)

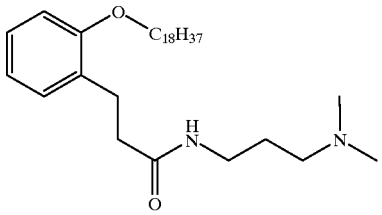

Potassium carbonate (0.55 g) and 1-bromooctadecane (0.67 g) were added to a solution containing N-[3-(dimethylamino)propyl]-3-(2-hydroxyphenyl)propanamide (0.50 g) obtained in Example 1(1) in acetone (5 ml). After being stirred for 24 hours at 60° C., the reaction mixture was concentrated. The residue, with ethyl acetate added thereto, was washed with water and brine successively, dried over sodium sulfate anhydride, and concentrated. The residue was purified by silica gel column chromatography (silica gel 40 g, chloroform: methanol=10:1), thereby yielding the entitled compound (0.42 g) as white solid.

$^1$H-NMR (CDCl$_3$) δ: 0.88 (3H, t, J=6.8 Hz), 1.2–1.4 (28H, m), 1.46 (2H, m),1.62 (2H, quintet, J=6.3 Hz), 1.80 (2H, quintet, J=6.6 Hz), 2.22 (6H, s), 2.33 (2H, t, J=6.3 Hz), 6.71 (1H, t, J=7.8 Hz), 2.94 (2H, t, J=7.8 Hz), 3.30 (2H, q, J=6.3 Hz), 3.96 (2H, t, J=6.6 Hz),6.71 n (1H, brt), 6.82 (1H, d, J=7.3 Hz), 6.85 (1H, td, J=7.3, 1.0 Hz), 7.15 (1H, d, J=7.3 Hz),7.16 (1H, td, J=7.3, 1.0 Hz).

Example 8

N-[3-(Dimethylamino)propyl]-3-[2-(octadecyloxy)phenyl]propanamide hydrochloride (Compound 8)

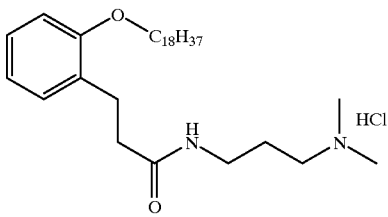

4N Hydrochloric acid/ethyl acetate solution (0.50 ml) was added to a solution containing N-[3-(dimethylamino)propyl]-3-[2-(octadecyloxy)phenyl]propanamide (0.42 g) in ethyl acetate (4 ml) at room temperature. After being stirred for 10 minutes, the reaction mixture was concentrated. The residue was recrystallized with the mixed solution of ethyl acetate-ethanol, thereby yielding the entitled compound (0.30 g) as white solid.

$^1$H-NMR (CDCl$_3$) δ: 0.88 (3H, t, J=6.8 Hz), 1.2–1.4 (28H, m), 1.47 (2H, m),1.82 (2H, m), 1.97 (2H, m), 2.57 (2H, t, J=7.3 Hz), 2.68 (6H, d, J=2.4 Hz), 2.75 (2H, m),2.97 (2H, t, J=7.3 Hz), 3.35 (2H, m), 3.99 (2H, t, J=6.6 Hz), 6.82 (1H, t, J=7.8 Hz), 6.84 (1H, d, J=7.8 Hz), 6.85 (1H, brt), 7.15 (1H, t, J=7.8 Hz), 7.16 (1H, d, J=7.8 Hz).

Example 9

N-(3-Morpholinopropyl)-3-[2-(octadecyloxy)phenyl]propanamide (Compound 9)

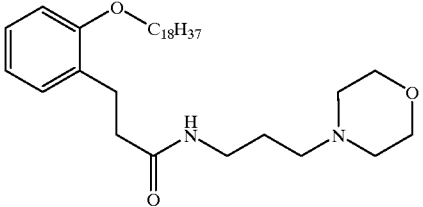

10% sodium hydroxide aqueous solution (7.21 g) was added to a solution containing 3-(2-hydroxyphenyl)-N-(3-morpholinopropyl)propanamide (2.60 g) obtained in Example 5(1) in dimethylsulfoxide (36 ml). The mixture was heated up to 80° C. and 1-bromooctadecane (2.97 g) was added thereto. After being stirred for 2.5 hours at 80° C., the reaction mixture, with water added thereto, was neutralized with 1N hydrochloric acid. The deposited solid was corrected by filtration and washed with water. This solid was purified by silica gel column chromatography (silica gel 100 g, chloroform:methanol=60:1 to 30:1), thereby yielding the entitled compound (1.99 g) as white solid.

$^1$H-NMR (CDCl$_3$) δ: 0.88 (3H, t, J=6.8 Hz), 1.2–1.4 (28H, m), 1.46 (2H, m), 1.59 (2H, quintet, J=6.4 Hz), 1.79 (2H, quintet, J=6.8 Hz), 2.35 (2H, t, J=6.4 Hz), 2.36 (4H, brt), 2.44 (2H, t, J=7.6 Hz), 2.96 (2H, t, J=7.6 Hz), 3.30 (2H, q, J=6.4 Hz), 3.65 (4H, t, J=4.6 Hz), 3.96 (2H, t, J=6.8 Hz), 6.57 (1H, brt), 6.82 (1H, d, J=7.8 Hz), 6.85 (1H, td, J=7.8, 1.0 Hz), 7.14 (1H, d, J=7.8 Hz), 7.16 (1H, td, J=7.8, 1.0 Hz).

Example 10

N-(3-Morpholinopropyl)-3-[2-(octadecyloxy)phenyl]propanamide hydrochloride (Compound 10)

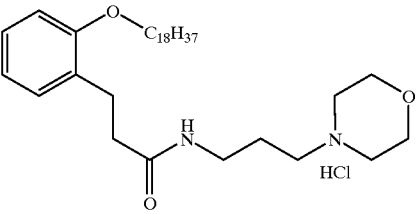

4N Hydrochloric acid/ethyl acetate solution (1.2 ml) was added to a solution containing N-(3-morpholinopropyl)-3-[2-(octadecyloxy)phenyl]propanamide (1.88 g) in ethyl acetate (38 ml) at room temperature. After being stirred for 45 minutes, the reaction mixture was concentrated. The residue was recrystallized with the mixed solution of ethyl acetate-ethanol, thereby yielding the entitled compound (1.89 g) as white solid.

$^1$H-NMR (CDCl$_3$) δ: 0.88 (3H, t, J=6.8 Hz), 1.2–1.4 (28H, m), 1.47 (2H, m), 1.82 (2H, quintet, J=6.8 Hz), 2.01 (2H, quintet, J=5.9 Hz), 2.55 (2H, t, J=7.3 Hz), 2.72 (2H, td, J=12.2, 3.4 Hz), 2.76 (2H, t, J=5.9 Hz), 2.96 (2H, t, J=7.3 Hz), 3.29 (2H, d, J=12.2 Hz), 3.34 (2H, q, J=5.9 Hz), 3.93 (2H, dd, J=12.2, 3.4 Hz), 3.99 (2H, t, J=6.8 Hz), 4.25 (2H, t, J=12.2 Hz), 6.80–6.84 (3H, m), 7.15 (1H, td, J=7.3, 2.0 Hz), 7.16 (1H, d, J=7.3 Hz), 12.53 (1H, brs).

Example 11

1-(4-Methylpiperazino)-3-[2-(octadecyloxy)phenyl]-1-propanone (Compound 11)

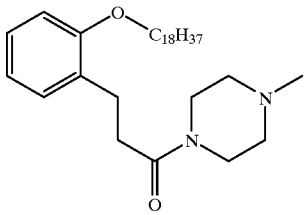

10% sodium hydroxide aqueous solution (6.70 g) was added to a solution containing 3-(2-hydroxyphenyl)-1-(4-methylpiperazino)-1-propanone (2.07 g) obtained in Example 3(1) in dimethylsulfoxide (21 ml). The mixture was heated up to 80° C. and 1-bromooctadecane (2.78 g) was added thereto. After being stirred for 3.75 hours at 80° C., the reaction mixture, with water added thereto, was neutralized with 1N hydrochloric acid. The deposited solid was corrected by filtration and washed with water. This solid was purified by silica gel column chromatography (silica gel 100 g, chloroform:methanol=50:1 to 10:1), thereby yielding the entitled compound (0.39 g) as white solid.

$^1$H-NMR (CDCl$_3$) δ: 0.88 (3H, t, J=6.8 Hz), 1.2–1.4 (28H, m), 1.44 (2H, m), 1.78 (2H, quintet, J=6.8 Hz), 2.26 (2H, t, J=4.9 Hz), 2.27 (3H, s), 2.34 (2H, t, J=4.9 Hz), 2.61 (2H, t, J=7.8 Hz), 2.94 (2H, t, J=7.8 Hz), 3.45 (2H, t, J=4.9 Hz), 3.64 (2H, t, J=4.9 Hz), 2.61 (2H, t, J=6.8 Hz), 6.82 (1H, d, J=8.3 Hz), 6.86 (1H, td, J=7.8, 1.0 Hz), 7.15–7.19 (2H, m).'

Example 12

1-(4-Methylpiperazino)-3-[2-(octadecyloxy)phenyl]-1-propanone hydrochloride (Compound 12)

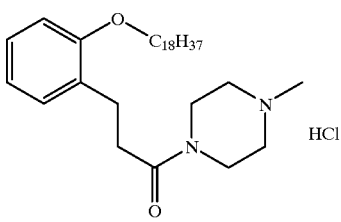

4N Hydrochloric acid/ethyl acetate solution (0.24 ml) was added to a solution containing 1-(4-methylpiperazino)-3-[2-(octadecyloxy)phenyl]-1-propanone (0.38 g) in ethyl acetate (4 ml) at room temperature. After being stirred for 15 minutes, the reaction mixture was concentrated. The residue was recrystallized with the mixed solution of ethyl acetate-ethanol, thereby yielding the entitled compound (0.38 g) as white solid.

$^1$H-NMR (CDCl$_3$) δ: 0.86 (3H, t, J=6.8 Hz), 1.2–1.4 (28H, m), 1.45 (2H, m), 1.79 (2H, quintet, J=6.8 Hz), 2.4–2.6 (3H, m), 2.63 (3H, s), 2.77 (1H, m), 2.91 (1H, m), 3.05 (1H, m), 3.14 (1H, m), 3.35 (2H, m), 3.75 (1H, m), 3.86 (1H, m), 3.98 (2H, t, J=6.8 Hz), 4.73 (1H, m), 6.85 (1H, d, J=7.3 Hz), 6.87 (1H, t, J=7.3 Hz), 7.14 (1H, dd, J=7.3, 1.5), 7.20 (1H, td, J=7.3, 1.5), 13.20 (1H, brs).

Example 13

2-[3-(4-Methylpiperazino)-3-oxopropyl]phenyl N-tetradecylcarbamate (Compound 13)

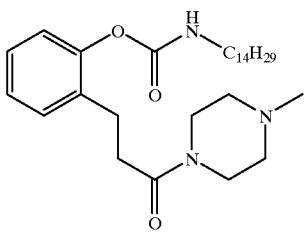

Triethylamine (1.06 ml) and tetradecyl isocyanate (1.64 g) were added to a solution containing 3-(2-hydroxyphenyl)-1-(4-methylpiperazino)-1-propanone (1.70 g) obtained in Example 3(1) in methylene chloride (17 ml). After being stirred for 18.5 hours at room temperature, the reaction mixture was diluted with chloroform, washed with saturated sodium hydrogencarbonate aqueous solution and brine successively, dried over sodium sulfate anhydride, and concentrated. The residue was purified by silica gel column chromatography (silica gel 100 g, chloroform:methanol= 60:1 to 30:1), thereby yielding the entitled compound (3.04 g) as white solid.

$^1$H-NMR (CDCl$_3$) δ: 0.88 (3H, t, J=6.8 Hz), 1.2–1.4 (22H, m), 1.57 (2H, m), 2.21 (2H, t, J=5.1 Hz), 2.26 (3H, s), 2.33 (2H, t, J=5.1 Hz), 2.57 (2H, t, J=7.8 Hz), 2.93 (2H, t, J=7.8 Hz), 3.25 (2H, q, J=6.7 Hz), 3.35 (2H, t, J=5.1 Hz), 3.63 (2H, t, J=5.1 Hz), 5.16 (1H, brt), 7.12 (2H, m), 7.22 (2H, m).

Example 14

2-[3-(4-Methylpiperazino)-3-oxopropyl]phenyl N-tetradecylcarbamate hydrochloride (Compound 14)

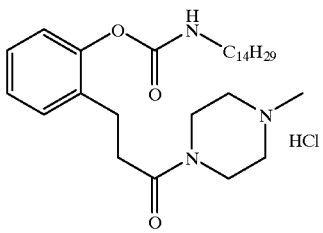

4N Hydrochloric acid/ethyl acetate solution (1.48 ml) was added to a solution containing 2-[3-(4-methylpiperazino)-3-oxopropyl]phenyl N-tetradecylcarbamate (2.40 g) in ethyl acetate (24 ml) while being cooled with ice. After being stirred for 45 minutes at room temperature, the reaction mixture was concentrated. The residue was recrystallized with the mixed solution of ethyl acetate-ethanol, thereby yielding the entitled compound (2.22 g) as white solid.

$^1$H-NMR (CDCl$_3$) δ: 0.88 (3H, t, J=6.8 Hz), 1.2–1.4 (22H, m), 1.59 (2H, m), 2.50 (2H, m), 2.57 (3H, s), 2.72 (1H, m), 2.98 (1H, m), 3.03 (2H, m), 3.2–3.4 (5H, m), 3.76 (2H, m), 4.69 (1H, d, J=14.7 Hz), 5.27 (1H, brt), 7.11 (1H, d, J=7.3 Hz), 7.15 (1H, t, J=7.3 Hz), 7.25 (2H, m), 12.91 (1H, brs).

Example 15

2-[3-(4-Benzylpiperazino)-3-oxopropyl]phenyl N-octadecylcarbamate (Compound 15)

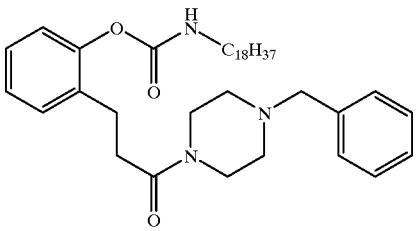

(1) 1-(4-Benzylpiperazino)-3-(2-hydroxyphenyl)-1-propanone

1-Benzylpiperazine (2.38 g) was added to 3,4-dihydrocoumarine (2.00 g) and stirred for 3 hours at 90° C., thereby yielding the entitled compound (4.77 g) as pale brown syrup.

$^1$H-NMR (CDCl$_3$) δ: 2.38 (4H, m), 2.69 (2H, t, J=5.4 Hz), 2.94 (2H, t, J=5.4 Hz), 3.40 (2H, t, J=5.1 Hz), 3.49 (2H, s), 3.62 (2H, t, J=5.1 Hz), 6.82 (1H, td, J=7.3, 1.0 Hz), 6.91 (1H, dd, J=7.3, 1.0 Hz), 7.04 (1H, dd, J=7.3, 1.0 Hz), 7.11 (1H, td, J=7.3, 1.0 Hz), 7.24–734 (5H, m), 9.57 (1H, brs).

(2) 2-[3-(4-Benzylpiperazino)-3-oxopropyl]phenyl N-octadecylcarbamate

Triethylamine (0.84 ml) and octadecyl isocyanate (1.88 ml) were added to a solution containing 1-(4-benzylpiperazino)-3-(2-hydroxyphenyl)-1-propanone (1.76 g) in methylene chloride (18 ml) and stirred for 17 hours at room temperature. The insoluble matters were filtrated out and washed with chloroform. The filtrate and washings were combined and the mixture was washed with saturated sodium hydrogencarbonate aqueous solution and brine successively, dried over sodium sulfate anhydride, and concentrated. The residue was purified by silica gel column chromatography (silica gel 75 g, chloroform:methanol=60:1), thereby yielding the entitled compound (2.32 g) as white solid.

$^1$H-NMR (CDCl$_3$) δ: 0.88 (3H, t, J=6.8 Hz), 1.2–1.4 (30H, m), 1.56 (2H, m), 2.25 (2H, t, J=4.9 Hz), 2.38 (2H, t, J=4.9 Hz), 2.56 (2H, t, J=7.8 Hz), 2.92 (2H, t, J=7.8 Hz), 3.23 (2H, td, J=6.4, 5.4 Hz), 3.34 (2H, t, J=4.9 Hz), 3.47 (2H, s), 3.62 (2H, t, J=4.9 Hz), 5.15 (1H, t, J=5.4 Hz), 7.12 (2H, m), 7.19–7.33 (7H, m).

Example 16

2-[3-(4-Benzylpiperazino)-3-oxopropyl]phenyl N-octadecylcarbamate hydrochloride (Compound 16)

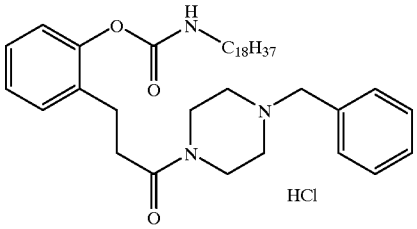

4N Hydrochloric acid/ethyl acetate solution (1.08 ml) was added to a solution containing 2-[3-(4-benzylpiperazino)-3-oxopropyl]phenyl N-octadecylcarbamate (2.21 g) in ethyl acetate (30 ml) at room temperature. After being stirred for 30 minutes, the reaction mixture was concentrated. The residue was recrystallized with the mixed solution of ethyl acetate-ethanol, thereby yielding the entitled compound (2.07 g) as white solid.

$^1$H-NMR (CDCl$_3$) δ: 0.88 (3H, t, J=6.8 Hz), 1.2–1.4 (30H, m), 1.58 (2H, m), 2.49 (1H, m), 2.55 (1H, m), 2.68 (1H, m), 2.94 (2H, m), 3.02 (2H, m), 3.19–3.26 (3H, m), 3.41 (1H, t, J=12.5 Hz), 3.73 (1H, d, J=13.7 Hz), 3.82–3.98 (3H, m), 4.64 (1H, d, J=14.7 Hz), 5.26 (1H, t, J=5.6 Hz), 7.10–7.14 (2H, m), 7.24 (2H, d, J=7.8 Hz), 7.44 (3H, m), 7.56 (2H, m), 12.98 (1H, brs).

Example 17

2-[2-(4-Methylpiperazino)-2-oxoethyl]phenyl N-octadecylcarbamate (Compound 17)

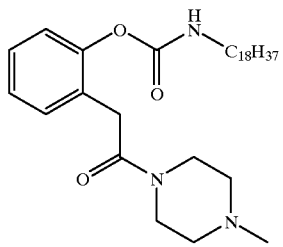

(1) 2-(2-Hydroxyphenyl)-1-(4-methylpiperazino)-1-ethanone

N-Methylpiperazine (1.52 g) was added to 2-coumaranone (2.01 g) and stirred for 3.5 hours at 85° C., thereby yielding the entitled compound (3.57 g) as pale brown solid.

$^1$H-NMR (CDCl$_3$) δ: 2.29 (3H, s), 2.37 (2H, t, J=4.9 Hz), 2.40 (2H, t, J=4.9 Hz), 3.66 (2H, t, J=4.9 Hz), 3.71 (2H, t, J=4.9 Hz), 3.74 (2H, s), 6.82 (1H, td, J=7.3, 1.5 Hz), 6.97 (1H, dd, J=7.3, 1.5 Hz), 7.01 (1H, dd, J=7.3, 1.5 Hz), 7.18 (1H, td, J=7.3, 1.5 Hz), 9.71 (1H, brs).

(2) 2-[2-(4-Methylpiperazino)-2-oxoethyl]phenyl N-octadecylcarbamate

Triethylamine (1.06 ml) and octadecyl isocyanate (2.35 ml) were added to a solution containing 2-(2-hydroxyphenyl)-1-(4-methylpiperazino)-1-ethanone (1.60 g) in methylene chloride (16 ml) and stirred for 15.5 hours at room temperature. The insoluble matters were filtrated out and washed with chloroform. The filtrate and washings were combined and the mixture was washed with saturated sodium hydrogencarbonate aqueous solution and brine successively, dried over sodium sulfate anhydride, and concentrated. The residue was purified by silica gel column chromatography (silica gel 100 g, chloroform:methanol=50:1 to 30:1), thereby yielding the entitled compound (3.23 g) as white solid.

$^1$H-NMR (CDCl$_3$) δ: 0.88 (3H, t, J=6.8 Hz), 1.2–1.4 (30H, m), 1.56 (2H, m), 2.19 (2H, t, J=4.9 Hz), 2.25 (3H, s), 2.35 (2H, t, J=4.9 Hz), 3.24 (2H, q, J=6.8 Hz), 3.40 (2H, t, J=4.9 Hz), 3.66 (2H, s & 2H, t, J=4.9 Hz), 5.20 (1H, brt), 7.14 (1H, d, J=7.3 Hz), 7.16 (1H, t, J=7.3 Hz), 7.24 (1H, d, J=7.3 Hz), 7.26 (1H, t, J=7.3 Hz).

Example 18

2-[2-(4-Methylpiperazino)-2-oxoethyl]phenyl N-octadecylcarbamate hydrochloride (Compound 18)

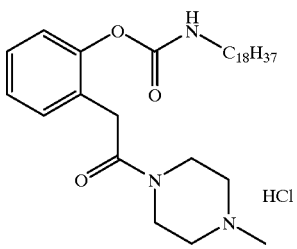

4N Hydrochloric acid/ethyl acetate solution (1.40 ml) was added to a solution containing 2-[2-(4-methylpiperazino)-2-oxoethyl]phenyl N-octadecylcarbamate (2.50 g) in ethyl acetate (25 ml) at room temperature. After being stirred for 30 minutes, the reaction mixture was concentrated. The residue was recrystallized with the mixed solution of ethyl acetate-ethanol, thereby yielding the entitled compound (2.52 g) as white solid.

$^1$H-NMR (CDCl$_3$) δ: 0.88 (3H, t, J=6.8 Hz), 1.2–1.4 (30H, m), 1.57 (2H, m), 2.20 (1H, m), 2.65 (3H, s), 2.83 (1H, m), 3.06 (1H, m), 3.22 (2H, m), 3.30 (1H, m), 3.42 (1H, m), 3.72 (2H, m), 3.88 (2H, m), 4.65 (1H, d, J=14.2 Hz), 5.40 (1H, brt), 7.13 (1H, d, J=7.8 Hz), 7.21 (1H, t, J=7.8 Hz), 7.27 (1H, d, J=7.8 Hz), 7.32 (1H, t, J=7.8 Hz), 12.93 (1H, brs).

| Preparation Example 1 Hair growth tonic | |
|---|---|
| Compound 3 | 0.5 wt % |
| Pyridoxine dioctanoate | 0.1 |
| Pantothenyl ethyl ether | 0.2 |
| Hinokitiol | 0.05 |
| Polyoxyethylene (12) polyoxypropylene (6) decyl tetradecyl | 1.0 |
| 1-Menthol | 0.1 |
| Disinfectants | Q.S. |
| 1,3-Butylene glycol | 3.0 |
| Ethanol | 70.0 |
| Purified water | Balance |

Preparation Method

Ethanol-soluble ingredients were dissolved into ethanol at room temperature while being stirred. Water-soluble ingredients were dissolved in purified water. The aqueous solution was added to the ethanol solution. After being homogeneously mixed, the mixture was filtrated.

| Preparation Example 2 Hair regrowth promoting liquid lotion | |
|---|---|
| Compound 4 | 0.2 wt % |
| Carpronium chloride | 1.0 |
| Pantothenyl ethyl ether | 0.5 |
| Diphenhydramine hydrochloride | 0.1 |
| Hinokitiol | 0.1 |
| dl-α-Tocopheryl acetate | 0.1 |
| Salicylic acid | 0.2 |
| 1-Menthol | 0.2 |
| Glycyrrhizinic acid | 0.1 |
| Sodium dl-pyrrolidonecarboxylate solution | 1.0 |
| Ethanol | 70.0 |
| Purified water | Balance |

Preparation Method

Ethanol-soluble ingredients were dissolved into ethanol at room temperature while being stirred. Water-soluble ingredients were dissolved in purified water. The aqueous solution was added to the ethanol solution. After being uniformly mixed, the mixture was filtrated.

| Preparation Example 3 Hair tonic | |
|---|---|
| Compound 8 | 0.1 wt % |
| Paeony root extract (1,3-butylene glycol extract) | 0.01 |
| Hinokitiol | 1.0 |
| Vitamin B$_6$ | 0.2 |
| Vitamin E acetate | 0.02 |
| Menthol | 0.2 |
| Swertia herb extract | 1.0 |
| Salicylic acid | 0.1 |
| Rosae rugosae flos extract (ethanol extract) | 0.5 |
| Propylene glycol | 2.0 |
| Sodium hyaluronate | 0.01 |
| Polyoxyethylene (10) monostearate | 2.0 |
| 75% Ethanol | Balance |

Preparation Method

Each of the above ingredients was successively added and dissolved into 75% ethanol with stirring to obtain a hair tonic.

| Preparation Example 4 Hair tonic | |
|---|---|
| Paeonia extract (ethanol extract) | 5.0 wt % |
| Compound 1 | 0.05 |
| Compound 2 | 0.05 |
| Hinokitiol | 1.0 |
| Vitamin B$_6$ | 0.2 |
| Vitamin E acetate | 0.02 |
| Menthol | 0.2 |
| Salicylic acid | 0.1 |
| Pueraria root extract (ethanol extract) | 0.5 |
| Propylene glycol | 2.0 |
| Sodium hyaluronate | 0.01 |
| Polyoxyethylene (10) monostearate | 2.0 |
| 75% Ethanol | Balance |

Preparation Method

Each of the above ingredients was successively added and dissolved into 75% ethanol with stirring to obtain a hair tonic.

| Preparation Example 5 Hair tonic | |
|---|---|
| Compound 3 | 0.05 wt % |
| 95% Ethanol | 50.0 |
| Monoammonium glycyrrhizinate | 0.05 |
| Paeonia extract (ethanol extract) | 0.05 |
| Paeony root extract (1,3-butylene glycol extract) | 0.02 |
| Saffron extract (ethanol extract) | 0.02 |
| Rosemary extract (ethanol extract) | 0.02 |
| Peppermint extract (ethanol extract) | 0.02 |
| Japanese angelica root extract (ethanol extract) | 0.02 |
| Althea extract (ethanol extract) | 0.02 |
| Rehmannia root extract (ethanol extract) | 0.02 |
| Coix extract (ethanol extract) | 0.02 |
| Sodium lauryl sulfate | 0.1 |
| N,N-Dimethyl-2-decyltetradecylamineoxide | 0.5 |
| Polyoxyethylene (40) hydrogenated castor oil | 0.5 |
| Succinic acid | Q.S. |
| Perfume and coloring agent | Q.S. |
| Purified water | Balance |

Preparation Method

A hair tonic was prepared according to Preparation Example 1.

| Preparation Example 6 Hair lotion | |
|---|---|
| 95% Ethanol | 90.0 wt % |
| Vitamin E acetate | 0.05 |
| Compound 9 | 0.01 |
| Sodium lauryl sulfate | 0.06 |
| Propylene glycol | 0.1 |
| Polyoxyethylene (40) hydrogenated castor oil | 0.5 |
| Lactic acid | Q.S. |
| Sodium lactate | Q.S. |
| Perfume and coloring agent | Q.S. |
| Purified water | Balance |

Preparation Method

Polyoxyethylene (40) hydrogenated castor oil and perfume were dissolved in 95% ethanol. Then, purified water and the other ingredients were successively added and dissolved into the mixture with stirring to obtain a transparent liquid lotion.

| Preparation Example 7 Hair tonic | |
|---|---|
| Compound 7 | 0.1 wt % |
| Hinokitiol | 1.0 |
| Vitamin B$_6$ | 0.2 |
| Vitamin E acetate | 0.02 |
| Menthol | 0.2 |
| Swertia herb extract | 1.0 |
| Salicylic acid | 0.1 |
| Propylene glycol | 2.0 |
| Polyoxyethylene (10) monostearate | 2.0 |
| 75% Ethanol | Balance |

Preparation Method

Each of the above ingredients was successively added and dissolved into 75% ethanol with stirring to obtain a hair tonic.

| Preparation Example 8 Hair tonic | |
|---|---|
| Compound 5 | 0.5 wt % |
| Compound 6 | 0.1 |
| Hinokitiol | 1.0 |
| Vitamin B$_6$ | 0.2 |
| Vitamin E | 0.02 |
| Menthol | 0.2 |
| Salicylic acid | 0.1 |
| Propylene glycol | 2.0 |
| Sodium hyaluronate | 0.01 |
| Polyoxyethylene (10 mol) monostearate | 2.0 |
| 70% Ethanol | Balance |

Preparation Method

Each of the above ingredients was successively added and dissolved into 70% ethanol with stirring to obtain a hair tonic.

| Preparation Example 9 O/W milky lotion | |
|---|---|
| (Phase A) | |
| Polyoxyethylene (60) hydrogenated castor oil | 2.0 wt % |
| Glycerin | 10.0 |
| Dipropylene glycol | 10.0 |
| 1,3-Butylene glycol | 4.0 |
| Compound 10 | 0.1 |
| Polyethylene glycol 1500 | 5.0 |
| (Phase B) | |
| Isocetyl octanoate | 10.0 |
| Squalane | 5.0 |
| Vaseline | 2.0 |
| Propyl paraben | 2.0 |
| (Phase C) | |
| 1% Carboxyvinylpolymer aqueous solution | 30.0 |
| Sodium hexametaphosphate | 0.03 |
| Ion-exchanged water | 8.35 |
| (Phase D) | |
| Ion-exchanged water | 4.5 |
| (Phase E) | |
| Potassium hydroxide | 0.12 |
| Ion-exchanged water | Balance |

Preparation Method

Phases A and B were heated and dissolved, separately. Both were mixed and treated with a homomixer, thereby obtaining a gel. Phase D was then gradually added to this gel and dispersed by the homomixer. Then, Phases C and E, which were mixed and dissolved in advance separately, were added to this gel dispersion successively. The mixture was emulsified by the homomixer to obtain an O/W milky lotion.

| Preparation Example 10 Cream | |
| --- | --- |
| (Phase A) | |
| N,N-Dimethyl-2-tetradecylamineoxide | 2.5 wt % |
| Liquid paraffin | 5.0 |
| Cetostearyl alcohol | 5.5 |
| Glyceryl monostealate | 3.0 |
| Polyoxyethylene (20) 2-octyldodecyl ether | 3.0 |
| Propyl paraben | 0.3 |
| Perfume | 0.1 |
| (Phase B) | |
| Compound 6 | 1.0 |
| Glycerin | 8.0 |
| Dipropylene glycol | 20.0 |
| Polyethylene glycol 4000 | 5.0 |
| Sodium hexametaphosphate | 0.005 |
| Ion-exchanged water | Balance |

Preparation Method

Phases A and B were heated and dissolved, separately. Both were mixed and emulsified by a homomixer to obtain a cream.

| Preparation Example 11 Aerosol spray | |
| --- | --- |
| (Stock solution) | |
| 95% Ethanol | 50.0 wt % |
| Glycyrrhizic acid | 0.1 |
| Compound 12 | 0.5 |
| Swertia herb extract | 0.1 |
| Sodium lauryl sulfate | 0.1 |
| Polyoxyethylene (40) hydrogenated castor oil | 0.5 |
| Lactic acid | Q.S. |
| Sodium lactate | Q.S. |
| Perfume | Q.S. |
| Ion-exchanged water | Balance |
| (Filling formulation) | |
| Stock solution | 50.0 |
| Liquefied petroleum gas | 50.0 |

Preparation Method

A stock solution was prepared by mixing and dissolving the ingredients of stock solution. This stock solution was filled into a can and a valve was fit thereto. Liquefied petroleum gas was filled into the can to obtain an aerosol spray.

| Preparation Example 12 Shampoo | | |
| --- | --- | --- |
| (1) | Sodium cocoylmethyltaurate | 2.0 wt % |
| (2) | Polyoxyethylene (8) oleyl ether | 2.0 |
| (3) | Lauric acid diethanolamide | 4.0 |
| (4) | Ethylene glycol fatty acid ester | 1.0 |
| (5) | Glycerin | 0.2 |
| (6) | Menthol | 0.1 |
| (7) | Compound 17 | 0.1 |
| (8) | Disodium edetate | 0.1 |
| (9) | Perfume | Q.S. |
| (10) | Purified water | Balance |

Preparation Method

The ingredient (10) was heated up to 70° C. The ingredients (1)–(9) were added to the heated ingredient (10) successively, and the mixture was mixed and dissolved with stirring. The mixture was cooled to obtain a shampoo.

| Preparation Example 13 Rinse | | |
| --- | --- | --- |
| (1) | Stearyl trimethyl ammonium chloride | 1.5 wt % |
| (2) | Dimethyl polysiloxane (20 cs) | 3.0 |
| (3) | Polyoxyethylene (10) oleyl ether | 1.0 |
| (4) | Glycerin | 5.0 |
| (5) | Compound 15 | 0.5 |
| (6) | 4-tert-Butyl-4'-methoxydibenzoylmethane | Q.S. |
| (7) | Ultraviolet absorber | Q.S. |
| (8) | Purified water | Balance |

Preparation Method

The water phase was prepared by adding the ingredients (1), (3) and (4) to the ingredient (8) and heating up to 70° C. The oil phase was prepared by heating and dissolving the other ingredients up to 70° C. The oil phase was added to the water phase and the mixture was mixed with stirring by an emulsifier. The mixture was cooled to obtain a rinse.

| Preparation Example 14 Scalp treatment | | |
| --- | --- | --- |
| (Stock solution) | | |
| (1) | Liquid paraffin | 27.0 wt % |
| (2) | Stearic acid | 5.0 |
| (3) | Cetanol | 5.0 |
| (4) | Sorbitan monooleate | 2.0 |
| (5) | Polyoxyethylene sorbitan monooleate | 3.0 |
| (6) | Compound 13 | 0.1 |
| (7) | 1,3-Butylene glycol | 5.0 |
| (8) | Antiseptic | Q.S. |
| (9) | Purified water | Balance |
| (Filling formulation) | | |
| Stock solution | | 50.0 |
| Liquefied petroleum gas | | 50.0 |

Preparation Method

The ingredients (5) and (6) were dissolved into ingredients (1) to (4). After being homogeneously dissolved with heating up to 80° C., the mixture was cooled down to 30° C. This mixture was added to the mixed solution of the ingredients (7) to (9), which was maintained at 30° C., and mixed with stirring to obtain a stock solution. This stock solution was filled into a can together with the liquefied petroleum gas to obtain a scalp treatment.

| Preparation Example 15 Scalp treatment | | |
| --- | --- | --- |
| (Stock solution) | | |
| (1) | Hinokitiol | 0.1 wt % |
| (2) | Swertia herb extract | 1.0 |
| (3) | Vitamin B$_6$ | 0.1 |
| (4) | Vitamin E | 0.01 |
| (5) | Menthol | 0.1 |
| (6) | Salicylic acid | 0.001 |
| (7) | Compound 8 | 0.1 |
| (8) | Polyoxyethylene sorbitan monooleate | 0.1 |
| (9) | Propylene glycol | 2.0 |
| (10) | 75% Ethanol | Balance |

-continued

Preparation Example 15 Scalp treatment (Filling formulation)

| | |
|---|---|
| Stock solution | 50.0 |
| Dimethyl ether | 50.0 |

Preparation Method

A scalp treatment was prepared according to Preparation Example 14.

In the following, the compounds and manufacturing processes thereof in accordance with the present invention are exemplified.

Compound 19
2-[3-[[3-(N-Methyl-N-phenylamino)propyl]amino]-3-oxopropyl]phenyl N-octadecyl-carbamate

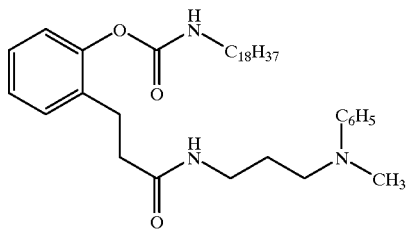

In Example 1(1), N-(3-aminopropyl)-N-methylaniline is used in place of N,N-dimethyl-1,3-propanediamine to give 3-(2-hydroxypheny)-N-[3-(N-methyl-N-phenylamino)propyl]propanamide.

In a similar manner to Example 1(2), the entitled compound is obtained from this compound and octadecyl isocyanate.

Compound 20
2-[3-[[5-(Dibenzylamino)pentyl]amino]-3-oxopropyl]phenyl N-octadecylcarbamate

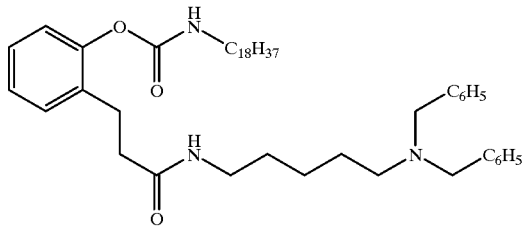

In Example 1(1), N,N-dibenzyl-1,5-pentanediamine is used in place of N,N-dimethyl-1,3-propanediamine to give N-[5-(dibenzylamino)pentyl]-3-(2-hydroxypheny)propanamide.

In a similar manner to Example 1(2), the entitled compound is obtained from this compound and octadecyl isocyanate.

Compound 21
4-Chloro-2-[3-[[3-(dimethylamino)propyl]amino]-3-oxopropyl]phenyl N-octadecylcarbamate

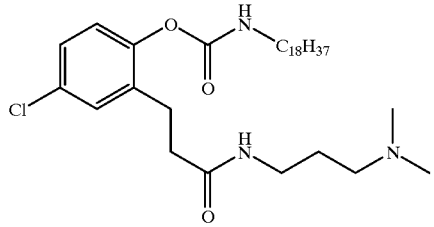

In Example 1(1), 6-choro-3,4-dihydrocoumarine is used in place of 3,4-dihydrocoumarine to give 3-(5-chloro-2-hydroxypheny)-N-[3-(dimethylamino)propyl]propanamide.

In a similar manner to Example 1(2), the entitled compound is obtained from this compound and octadecyl isocyanate.

Also, by using 3,4-dihydrocoumarine having a corresponding substituent $R^4$ in place of 3,4-dihydrocoumarine, a reaction is effected according to the manufacturing method of said Compound 21 to give the following Compounds 22 to 32.

Compound 22
2-[3-[[3-(Dimethylamino)propyl]amino]-3-oxopropyl]-3-methylphenyl N-octadecylcarbamate

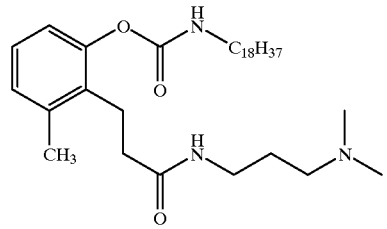

Compound 23
3-Acetyl-2-[3-[[3-(dimethylamino)propyl]amino]-3-oxopropyl]phenyl N-octadecylcarbamate

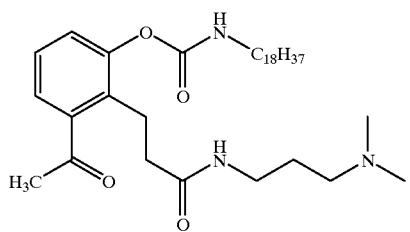

Compound 24
2-[3-[[3-(Dimethylamino)propyl]amino]-3-oxopropyl]-5-nitrophenyl N-octadecylcarbamate

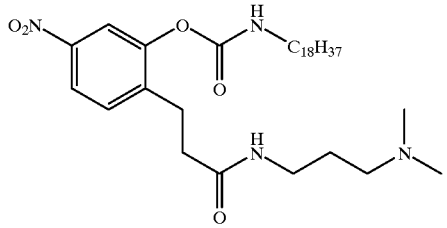

Compound 25

2-[3-[[3-(Dimethylamino)propyl]amino]-3-oxopropyl]-5-methoxyphenyl N-octadecylcarbamate

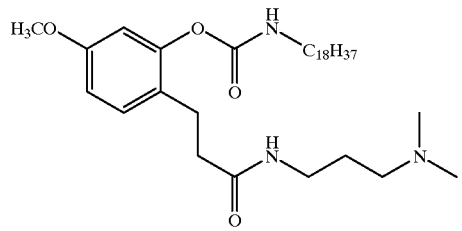

Compound 26

5-Cyano-2-[3-[[3-(dimethylamino)propyl]amino]-3-oxopropyl]phenyl N-octadecylcarbamate

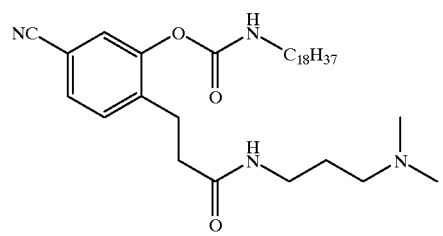

Compound 27

2-[3-[[3-(Dimethylamino)propyl]amino]-3-oxopropyl]-4-methoxycarbonylphenyl N-octadecylcarbamate

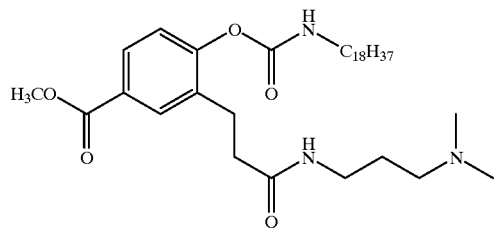

Compound 28

4-Carbamoyl-2-[3-[[3-(dimethylamino)propyl]amino]-3-oxopropyl]phenyl N-octadecylcarbamate

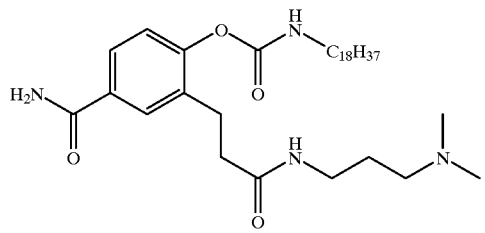

Compound 29

2-[3-[[3-(Dimethylamino)propyl]amino]-3-oxopropyl]-4-methylcarbamoylphenyl N-octadecylcarbamate

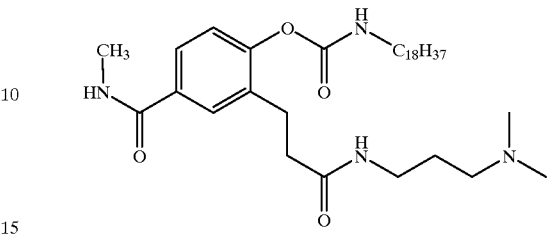

Compound 30

5-Dimethylamino-2-[3-[[3-(dimethylamino)propyl]amino]-3-oxopropyl]phenyl N-octadecylcarbamate

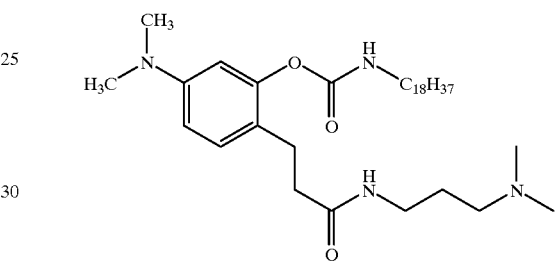

Compound 31

5-Benzoylamino-2-[3-[[3-(dimethylamino)propyl]amino]-3-oxopropyl]phenyl N-octadecylcarbamate

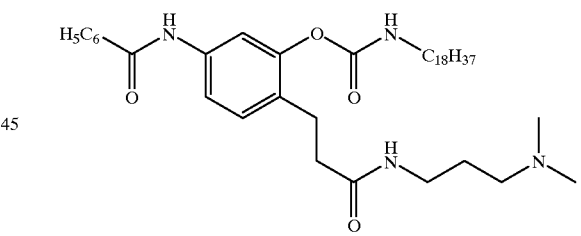

Compound 32

3-Acetoxy-2-[3-[[3-(dimethylamino)propyl]amino]-3-oxopropyl]phenyl N-octadecylcarbamate

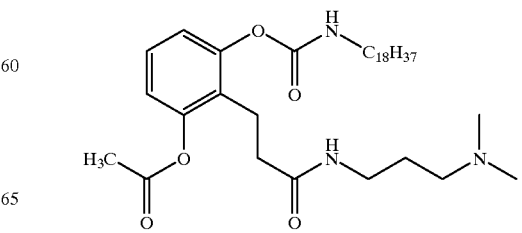

Compound 33
N-[3-(Dimethylamino)propyl]-N-methyl-3-[2-(octadecyloxy)phenyl]propanamide

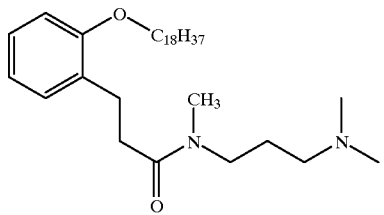

In Example 1(1), N,N,N'-trimethyl-1,3-propanediamine is used in place of N,N-dimethyl-1,3-propanediamine to give N-[3-dimethylamino)propyl]-N-methyl-3-(2-hydroxypheny)propanamide.

In a similar manner to Example 7, the entitled compound is obtained from this compound and 1-bromooctadecane.

Compound 34
2-[3-[N-Acetyl-N-[3-(dimethylamino)propyl]amino]-3-oxopropyl]phenyl N-acetyl-N-octadecylcarbamate

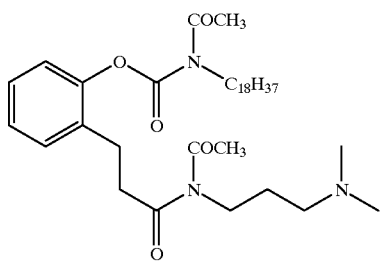

Compound 1 obtained in Example 1 is acetylated to give the entitled compound.

Compound 35
2-[3-[N-[3-(Dimethylamino)propyl]-N-(methylcarbamoyl)amino]-3-oxopropyl]phenyl N-methylcarbamoyl-N-octa

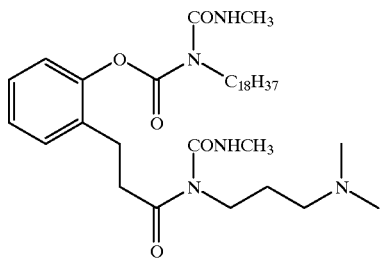

Compound 1 obtained in Example 1 is methylcarbamoylated to give the entitled compound.

Compound 36
2-(3-Octadecylamino-3-oxopropyl)phenyl N-[3-(dimethylamino)propyl]carbamate

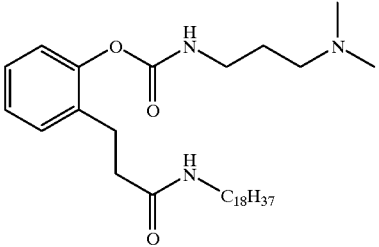

In Example 1(1), octadecylamine is used in place of N,N-dimethyl-1,3propanediamine to give 3-(2-hydroxypheny)-N-octadecylpropanamide.

This compound reacts with phenyl chlorocarbonate in chloroform in the presence of pyridine and then reacts with N,N-dimethyl-1,3-propanediamine to give the entitled compound.

Compound 37
2-(3-Octadecylamino-3-oxopropyl)phenyl (4-methylpiperazino)carboxylate

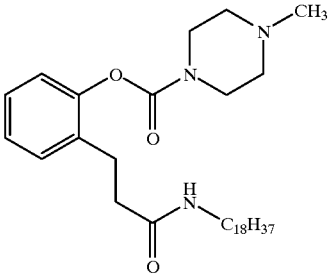

In Example 1(1), octadecylamine is used in place of N,N-dimethyl-1,3-propanediamine to give 3-(2-hydroxypheny)-N-octadecylpropanamide.

This compound reacts with phenyl chlorocarbonate in chloroform in the presence of pyridine and then reacts with 1-methylpiperazine to give the entitled compound.

Compound 38
2-(3-Octadecylamino-3-oxopropyl)phenyl N-(dimethylamino)carbamate

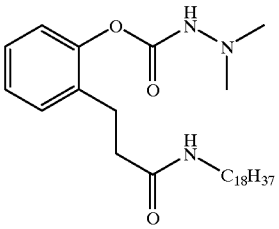

In Example 1(1), octadecylamine is used in place of N,N-dimethyl-1,3-propanediamine to give 3-(2-hydroxypheny)-N-octadecylpropanamide.

This compound reacts with phenyl chlorocarbonate in chloroform in the presence of pyridine and then reacts with 1,1-dimethylhydrazine to give the entitled compound.

Compound 39
2-(3-Octadecylamino-3-oxopropyl)phenyl N-(2-aminoethyl)carbamate

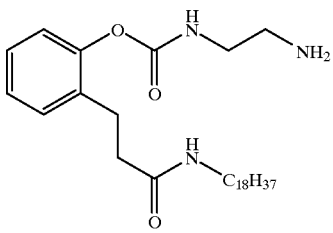

In Example 1(1), octadecylamine is used in place of N,N-dimethyl-1,3-propanediamine to give 3-(2-hydroxypheny)-N-octadecylpropanamide.

This compound reacts with phenyl chlorocarbonate in chloroform in the presence of pyridine and then reacts with ethylenediamine to give the entitled compound.

Compound 40
3-[2-[4-(Dimethylamino)butoxy]phenyl]-N-octadecylpropanamide

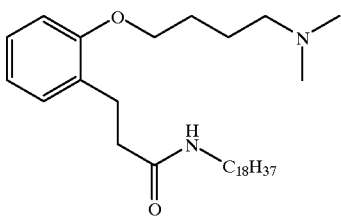

In Example 1(1), octadecylamine is used in place of N,N-dimethyl-1,3-propanediamine to give 3-(2-hydroxypheny)-N-octadecylpropanamide.

This compound reacts with 1-bromo-4-chlorobutane in acetone in the presence of potassium carbonate at the reflux temperature to give 3-[2-(4-chlorobutoxy)phenyl]-N-octadecylpropanamide.

This compound reacts with dimethylamine in acetone in the presence of potassium carbonate at the reflux temperature to give the entitled compound.

Compound 41
N-Octadecyl-3-[2-(4-piperizinobutoxy)phenyl]propanamide

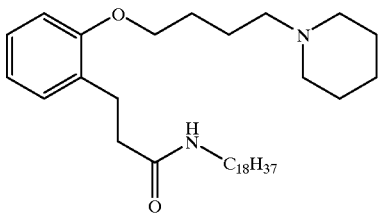

In Example 1(1), octadecylamine is used in place of N,N-dimethyl-1,3-propanediamine to give 3-(2-hydroxypheny)-N-octadecylpropanamide.

This compound reacts with 1-bromo-4-chlorobutane in acetone in the presence of potassium carbonate at the reflux temperature to give 3-[2-(4-chlorobutoxy)phenyl]-N-octadecylpropanamide.

This compound reacts with piperidine in acetone in the presence of potassium carbonate at the reflux temperature to give the entitled compound.

Compound 42
2-[3-[[3-(Dimethylamino)propyl]amino-3-oxopropyl]phenyl octadecanoate

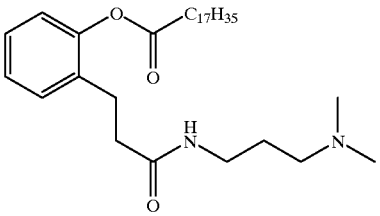

DCC is added to a solution containing N-[3-(dimethylamino)propyl]-3-(hydroxyphenyl)propanamide and stearic acid in N,N-dimethylformamide and reacted at room temperature to give the entitled compound.

Compound 43
2-[3-(Octadecylamino)-3-oxopropyl]phenyl]3-(dimethylamino)propionate

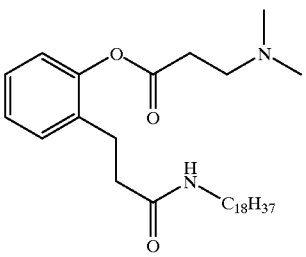

In Example 1(1), octadecylamine is used in place of N,N-dimethyl-1,3-propanediamine to give 3-(2-hydroxypheny)-N-octadecylpropanamide.

DCC is added to a solution containing this compound and 3-(dimethylamino)propionic acid in N,N-dimethylformamide and reacted at room temperature to give the entitled compound.

What is claimed is:

1. A (2-substituted oxyphenyl)alkanamide derivative or a salt thereof expressed by the following Formula (I-1):

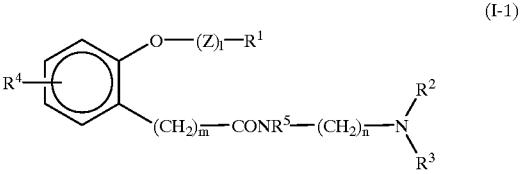

(I-1)

wherein
Z is —CO— or —CONR$^6$—;
R$^1$ is a hydrocarbon group of C$_{3-30}$;
R$^2$ and R$^3$ individually represent a hydrogen atom, a lower alkyl group or a benzyl group;
R$^4$ is selected from the group consisting of a hydrogen atom, a halogen atom, a lower alkyl group, a lower acyl group, a nitro group, a cyano group, a lower alkoxycarbonyl group, a carbamoyl group, a lower alkylcarbamoyl group, a lower alkylamino group, a lower acylamino group, a lower alkoxy group and a lower acyloxy group;

$R^5$ is a hydrogen atom, a lower alkyl group, a lower acyl group or a lower alkylcarbamoyl group;

$R^6$ is a hydrogen atom, a lower alkyl group, a lower acyl group or a lower alkylcarbamoyl group;

l is 0 or 1;

m is 1 or 2; and n is an integer of 0–5.

2. A (2-substituted oxyphenyl)alkanamide derivative or a salt thereof according to claim 1, wherein $R^5$ is a hydrogen atom.

3. A (2-substituted oxyphenyl)alkanamide derivative or a salt thereof according to claim 2, wherein $R^2$ and $R^3$ are lower alkyl groups.

4. A (2-substituted oxyphenyl)alkanamide derivative or a salt thereof according to claim 1, wherein l is 1 and Z is —CONR$^6$—.

5. A (2-substituted oxyphenyl)alkanamide derivative or a salt thereof according to claim 1, wherein l is 0.

6. A (2-substituted oxyphenyl)alkanamide derivative or a salt thereof according to claim 1, wherein $R^1$ is an alkyl group of $C_{10-30}$.

7. A (2-substituted oxyphenyl)alkanamide derivative or a salt thereof according to claim 1, wherein $R^4$ is a hydrogen atom.

8. A (2-substituted oxyphenyl)alkanamide derivative or a salt thereof according to claim 1, wherein n is an integer of 2–5.

9. A hair growth promoting composition comprising an effective amount of the (2-substituted oxyphenyl) alkanamide derivative or the pharmacologically acceptable salt thereof according to claim 1.

10. An external preparation for skin comprising the (2-substituted oxyphenyl)alkanamide derivative or the pharmacologically acceptable salt thereof according to claim 1.

11. A method for promoting hair growth, which comprises applying an effective amount of the (2-substituted oxyphenyl)alkanamide derivative or the pharmacologically acceptable salt thereof according to claim 1 on skin of mammals.

12. A method for promoting hair growth according to claim 11, wherein the skin of mammals is human scalp.

* * * * *